(12) United States Patent
Davis et al.

(10) Patent No.: US 10,420,709 B2
(45) Date of Patent: Sep. 24, 2019

(54) DOSING CONTROL COUPLING FOR ENTERAL FLUID TRANSFER

(71) Applicant: NEOMED, INC., Woodstock, GA (US)

(72) Inventors: Benjamin M. Davis, Woodstock, GA (US); Aaron N. Ingram, Canton, GA (US); Duane Webb, Roswell, GA (US); Mariann Cary, Canton, GA (US)

(73) Assignee: NeoMed, Inc., Woodstock, GA (US)

( * ) Notice: Subject to any disclaimer, the term of this patent is extended or adjusted under 35 U.S.C. 154(b) by 412 days.

(21) Appl. No.: 15/210,282

(22) Filed: Jul. 14, 2016

(65) Prior Publication Data

US 2016/0317393 A1  Nov. 3, 2016

Related U.S. Application Data

(60) Provisional application No. 62/192,454, filed on Jul. 14, 2015, provisional application No. 62/207,120, (Continued)

(51) Int. Cl.
*A61J 15/00* (2006.01)
*A61M 5/34* (2006.01)
(Continued)

(52) U.S. Cl.
CPC ......... *A61J 15/0026* (2013.01); *A61J 7/0053* (2013.01); *A61M 5/3134* (2013.01);
(Continued)

(58) Field of Classification Search
CPC ............... A61J 15/0026; A61J 15/0076; A61J 15/0084; A61J 15/0088; A61J 15/1475;
(Continued)

(56) References Cited

U.S. PATENT DOCUMENTS 1,704,921 A   3/1929  Nicoll
2,708,438 A   5/1955  Cohen
(Continued)

FOREIGN PATENT DOCUMENTS

CA    2548976 A1   12/2007
DE    2108381 A1    8/1972
(Continued)

OTHER PUBLICATIONS

Written Opinion for PCT/US2016/042248; dated Jul. 11, 2017; 8 pgs.
(Continued)

*Primary Examiner* — Kami A Bosworth
*Assistant Examiner* — Alexandra Lalonde
(74) *Attorney, Agent, or Firm* — NeoMed, Inc.

(57) ABSTRACT

An enteral dosing control coupling comprising a cylindrical collar defining a hollow internal chamber and a lumen extension tip projecting axially into the internal chamber, the lumen extension tip defining an internal lumen extending therethrough. In example forms, the lumen extension tip is integrally formed with the cylindrical collar. In other example forms, the lumen extension tip is a separate piece and is removably engageable within the cylindrical collar.

11 Claims, 14 Drawing Sheets

Related U.S. Application Data filed on Aug. 19, 2015, provisional application No. 62/350,934, filed on Jun. 16, 2016.

(51) Int. Cl.
| | | |
|---|---|---|
| *A61J 7/00* | (2006.01) | |
| *A61M 5/31* | (2006.01) | |
| *A61M 39/10* | (2006.01) | |
| *A61M 39/12* | (2006.01) | |

(52) U.S. Cl.
CPC ........ *A61M 5/345* (2013.01); *A61M 39/1011* (2013.01); *A61M 39/12* (2013.01); *A61M 2039/1077* (2013.01); *A61M 2039/1094* (2013.01)

(58) Field of Classification Search
CPC ........ A61J 7/053; A61J 7/0053; A61J 1/1475; A61M 5/3134; A61M 5/345; A61M 2039/1094; A61M 5/1782; A61M 5/178; A61M 5/3129; A61M 39/1011; A61M 39/12; A61M 39/10; A61M 2039/1077; A61M 2039/1083; A61M 2039/1088
See application file for complete search history.

(56) References Cited

U.S. PATENT DOCUMENTS

| | | | |
|---|---|---|---|
| 2,869,543 | A | 1/1959 | Ratcliff et al. |
| 2,939,459 | A | 6/1960 | Lazarte et al. |
| 3,326,215 | A | 6/1967 | Sarnoff et al. |
| 3,370,754 | A | 2/1968 | Cook et al. |
| 3,489,147 | A | 1/1970 | Shaw |
| 3,557,787 | A | 1/1971 | Cohen |
| 3,570,486 | A | 3/1971 | Engelsher et al. |
| 3,572,337 | A | 3/1971 | Schunk |
| 3,678,931 | A | 7/1972 | Cohen |
| 3,680,558 | A | 8/1972 | Kapelowitz |
| 3,682,174 | A | 8/1972 | Cohen |
| 3,684,136 | A | 8/1972 | Baumann |
| 3,685,514 | A | 8/1972 | Cheney |
| 3,756,390 | A | 9/1973 | Abbey et al. |
| 3,885,562 | A | 5/1975 | Lampkin |
| 3,885,710 | A | 5/1975 | Cohen |
| 3,896,805 | A | 7/1975 | Weingarten |
| 3,921,633 | A | 11/1975 | Tischlinger |
| 4,046,145 | A | 9/1977 | Choksi et al. |
| 4,171,699 | A | 10/1979 | Jones et al. |
| 4,254,768 | A | 3/1981 | Ty |
| 4,351,334 | A | 9/1982 | Inglefield, Jr. |
| D267,536 | S | 1/1983 | Findlay |
| 4,464,174 | A | 8/1984 | Ennis |
| D282,807 | S | 3/1986 | Hasse |
| D287,877 | S | 1/1987 | Holewinski et al. |
| 4,639,248 | A | 1/1987 | Schweblin |
| 4,693,706 | A | 9/1987 | Ennis, III |
| 4,702,737 | A | 10/1987 | Pizzino |
| D320,084 | S | 9/1991 | Stewart et al. |
| D323,031 | S | 1/1992 | Ahlstrand et al. |
| 5,115,816 | A | 5/1992 | Lee |
| D330,862 | S | 11/1992 | Shibley et al. |
| 5,176,415 | A | 1/1993 | Choksi |
| 5,188,599 | A | 2/1993 | Botich et al. |
| 5,279,566 | A | 1/1994 | Kline, Jr. et al. |
| 5,286,067 | A | 2/1994 | Choksi |
| 5,372,586 | A | 12/1994 | Haber et al. |
| 5,395,345 | A | 3/1995 | Gross |
| D369,214 | S | 4/1996 | Nason |
| 5,533,973 | A | 7/1996 | Piontek et al. |
| 5,569,193 | A | 10/1996 | Hofsetter et al. |
| D383,205 | S | 9/1997 | Pagay et al. |
| 5,704,918 | A | 1/1998 | Higashikawa |
| 5,779,668 | A | 7/1998 | Grabenkort |
| 5,785,682 | A | 7/1998 | Grabenkort |
| 5,836,919 | A | 11/1998 | Skurka et al. |
| 5,843,042 | A | 12/1998 | Ren |
| 5,876,379 | A | 3/1999 | Beauvais et al. |
| 6,010,481 | A | 1/2000 | Lee |
| D420,129 | S | 2/2000 | McMahon |
| 6,126,644 | A | 10/2000 | Naganuma et al. |
| 6,164,044 | A | 12/2000 | Porfano et al. |
| 6,165,153 | A * | 12/2000 | Kashmer ............ A61M 5/5013 604/110 |
| D436,661 | S | 1/2001 | Berry |
| D445,176 | S | 7/2001 | Landers |
| 6,270,519 | B1 | 8/2001 | Botts |
| D447,797 | S | 9/2001 | Odell et al. |
| 6,391,008 | B1 | 5/2002 | Tsai |
| D460,820 | S | 7/2002 | Niedospial, Jr. |
| D461,243 | S | 8/2002 | Niedospial, Jr. |
| 6,432,087 | B1 | 8/2002 | Hoeck et al. |
| D462,761 | S | 9/2002 | Swenson |
| D463,025 | S | 9/2002 | Swenson |
| 6,544,233 | B1 | 4/2003 | Fukui et al. |
| 6,689,106 | B2 | 2/2004 | Bush, Jr. et al. |
| 6,752,782 | B2 | 6/2004 | Liao |
| D504,512 | S | 4/2005 | Fournier |
| D505,200 | S | 5/2005 | Simpson et al. |
| 6,972,004 | B2 | 12/2005 | La |
| 6,991,618 | B2 | 1/2006 | Lau et al. |
| 7,018,089 | B2 | 3/2006 | Wenz et al. |
| 7,172,085 | B2 | 2/2007 | Beaudette |
| D542,406 | S | 5/2007 | Knight et al. |
| D552,773 | S | 10/2007 | Greenberg |
| 7,322,941 | B2 | 1/2008 | Henshaw |
| D578,210 | S | 10/2008 | Muta et al. |
| D581,048 | S | 11/2008 | Kawamura |
| 7,455,661 | B2 | 11/2008 | Barrelle et al. |
| D593,801 | S | 6/2009 | Wilson et al. |
| 7,713,245 | B2 | 5/2010 | Cipoletti et al. |
| D618,347 | S | 6/2010 | Bradshaw |
| 7,842,217 | B2 | 11/2010 | Enns et al. |
| D632,144 | S | 2/2011 | Weisenbach |
| 7,879,002 | B2 | 2/2011 | Jessop |
| D635,249 | S | 3/2011 | Becker |
| 7,951,108 | B2 | 5/2011 | Harper et al. |
| 8,016,795 | B2 | 9/2011 | Barrelle et al. |
| D646,531 | S | 10/2011 | Murphy |
| D649,242 | S | 11/2011 | Kosinski et al. |
| D650,903 | S | 12/2011 | Kosinski et al. |
| 8,070,721 | B2 | 12/2011 | Kakish et al. |
| 8,075,523 | B2 | 12/2011 | Wayman et al. |
| D675,540 | S | 2/2013 | Montminy |
| 8,398,601 | B2 | 3/2013 | Smith et al. |
| 8,465,461 | B2 | 6/2013 | Wu et al. |
| D690,417 | S | 9/2013 | Solomon |
| 8,540,683 | B2 | 9/2013 | Williams, Jr. et al. |
| 8,740,858 | B2 | 6/2014 | Kawamura |
| 8,784,377 | B2 | 7/2014 | Ranalletta et al. |
| D713,028 | S | 9/2014 | Yevmenenko |
| D715,428 | S | 10/2014 | Baid |
| 8,870,833 | B2 | 10/2014 | Lloyd et al. |
| D721,803 | S | 1/2015 | Dubach |
| 8,936,577 | B2 | 1/2015 | Lee et al. |
| 8,945,182 | B2 | 2/2015 | Oates, II et al. |
| 8,992,505 | B2 | 3/2015 | Thorne, Jr. et al. |
| D726,305 | S | 4/2015 | Furukawa |
| 9,060,918 | B1 | 6/2015 | Tomassini |
| D739,524 | S | 9/2015 | Zemel et al. |
| 9,149,622 | B2 | 10/2015 | Bonnet et al. |
| D743,025 | S | 11/2015 | Berler |
| 9,272,099 | B2 | 3/2016 | Limaye et al. |
| 9,345,638 | B2 | 5/2016 | Ferrara |
| 9,408,971 | B2 | 8/2016 | Carlyon |
| 9,408,981 | B2 | 8/2016 | Cowan |
| 9,433,768 | B2 | 9/2016 | Tekeste et al. |
| D773,042 | S | 11/2016 | Hwang et al. |
| 9,522,237 | B2 | 12/2016 | Alheidt et al. |
| D785,162 | S | 4/2017 | Swisher et al. |
| D792,969 | S | 7/2017 | Taylor |
| 9,814,870 | B2 | 11/2017 | Jin et al. |
| 9,839,750 | B2 | 12/2017 | Limaye et al. |
| 2002/0151851 | A1 | 10/2002 | Fu |

(56) References Cited

U.S. PATENT DOCUMENTS

| | | |
|---|---|---|
| 2003/0034264 A1 | 2/2003 | Hamai et al. |
| 2003/0199816 A1 | 10/2003 | Ramming |
| 2005/0038395 A1 | 2/2005 | Shih |
| 2005/0177100 A1 | 8/2005 | Harper et al. |
| 2005/0251096 A1 | 11/2005 | Armstrong et al. |
| 2006/0161106 A1 | 7/2006 | Wu |
| 2006/0189932 A1 | 8/2006 | Yang et al. |
| 2006/0264824 A1 | 11/2006 | Swisher, III |
| 2007/0005014 A1 | 1/2007 | Lin et al. |
| 2007/0123822 A1 | 5/2007 | Wang et al. |
| 2008/0021414 A1 | 1/2008 | Alheidt |
| 2008/0045929 A1 | 2/2008 | Birnbach |
| 2008/0114307 A1 | 5/2008 | Smith et al. |
| 2008/0140020 A1 | 6/2008 | Shirley |
| 2012/0022457 A1 | 1/2012 | Silver |
| 2012/0029471 A1 | 2/2012 | Lee et al. |
| 2012/0150129 A1* | 6/2012 | Jin .................. A61M 39/10 604/240 |
| 2012/0245564 A1* | 9/2012 | Tekeste ............. A61M 5/3134 604/535 |
| 2012/0265150 A1 | 10/2012 | Frey et al. |
| 2013/0030379 A1 | 1/2013 | Ingram et al. |
| 2013/0090606 A1 | 4/2013 | Shams |
| 2013/0098861 A1 | 4/2013 | Lair et al. |
| 2013/0144255 A1 | 6/2013 | Cohn |
| 2013/0150797 A1 | 6/2013 | Lesch, Jr. |
| 2014/0276442 A1 | 9/2014 | Haughey |
| 2015/0073356 A1 | 3/2015 | Sasayama et al. |
| 2015/0164744 A1 | 6/2015 | Ingram et al. |
| 2015/0238747 A1* | 8/2015 | Russo ............... A61M 39/1011 604/533 |
| 2016/0030293 A1 | 2/2016 | Dorsey et al. |
| 2016/0067422 A1 | 3/2016 | Davis et al. |
| 2016/0159635 A1 | 6/2016 | Davis et al. |
| 2016/0175201 A1 | 6/2016 | Schuessler |
| 2016/0199591 A1 | 7/2016 | Matsui |
| 2016/0250415 A1 | 9/2016 | Yagi et al. |
| 2017/0203045 A1 | 7/2017 | Ivosevic et al. |
| 2018/0014998 A1* | 1/2018 | Yuki .................. A61M 5/34 |
| 2018/0326198 A1* | 11/2018 | Yuki .................. A61M 39/1011 |

FOREIGN PATENT DOCUMENTS

| | | |
|---|---|---|
| EP | 0148715 A1 | 7/1985 |
| EP | 1110568 A2 | 6/2001 |
| EP | 1447072 A1 | 8/2004 |
| EP | 1980282 A1 | 10/2008 |
| EP | 2269685 A2 | 1/2011 |
| FR | 1126718 A | 11/1956 |
| FR | 2720279 A1 | 12/1995 |
| FR | 2929854 A1 | 10/2009 |
| FR | 2930428 A1 | 10/2009 |
| WO | 9200717 A1 | 1/1992 |
| WO | 9803210 A2 | 1/1998 |
| WO | 9831410 A1 | 7/1998 |
| WO | 0130415 A2 | 5/2001 |
| WO | 03072162 A2 | 9/2003 |
| WO | 2011026156 A1 | 3/2011 |
| WO | 2013081699 A2 | 6/2013 |
| WO | 2016154304 A1 | 9/2016 |
| WO | 2016205626 A1 | 12/2016 |
| WO | 2017011754 A1 | 1/2017 |

OTHER PUBLICATIONS

Kasper et al.; "ENFit Enteral Connections: Are You Ready?"; Premier Safety Institute; Mar. 26, 2015; 5 pgs.

Invitation to Pay Additional Fees for PCT/US2017/052321; dated Dec. 4, 2017; 10 pgs.

Guide to New Enteral Feeding Connections; Covidien; Dec. 31, 2015; 4 pgs.

Invitation to Pay Additional Fees for PCT/US2017/042559; dated Oct. 16, 2017; 15 pgs.

Alternative Syringes Low Displacement Option PowerPoint Presention; Presented by Rork Swisher of Covidien; ISO 80369 Series Meeting; Berlin Germany; 11 pgs; Mar. 19, 2014.pgs.

Bostik Evo-Stik Adhesive Express Syringe; www.amazon.co.uk/Bostik-808546-Evo-Stik-Adhesive-Express/dp/B006O6DMFO; 1 pg; date unknown.

Brazilian Peel Syringe Applicator; www.amazon.com/Brazilian-Peel-Applications/dp/B003IIUN6W/ref=cm_cr_pr_product_top?ie=UTF8; 1 pg; date unknown.

International Search Report & Written Opinion for PCT/US2011/051338; dated Dec. 14, 2011; 20 pgs.

International Search Report & Written Opinion for PCT/US2016/023771; dated Jun. 27, 2016; 17 pgs.

NeoMed Enteral Syringe; 2007 (8 pgs).

New ISO Tubing Connector Standards: A Follow-Up to the Sentinel Event Alert Webinar PowerPoint Presention; www.jointcommission.org; 50 pgs; Dec. 3, 2014.

New Tube Feeding Connectors Webinar PowerPoint Presention; www.oley.org; 24 pgs; Jun. 24, 2014.

Sulzer Dosing Syringe with Piston; www.directindustry.com/prod/sulzer-chemtech/product-28889-903259.html; 1 pg; date unknown.

Vygon Sales Sheet; 2014 (2 pgs).

International Search Report & Written Opinion for PCT/US2017/043747; dated Nov. 2, 2017; 14 pgs.

"Enfit Update"; Feeding Tube Awareness Foundation; Feb. 2015; 5 pgs.

Pash, Elizabeth MS, RD, LDN; "Enteral Connectors: New Standards and Designs"; DNS Symposium; Baltimore, Maryland; Jun. 2015; 32 pgs.

Carrera, Amy Long, MS, RD, CNSC, CWCMS; Enfit: How to Transition to the New Feeding Tube Connectors; Shield Healthcare, Inc.; Feb. 4, 2015; 5 pgs.

International Search Report & Written Opinion for PCT/US2016/042248; dated Sep. 21, 2016; 10 pgs.

Premier Safety Institute; New Enteral Feeding Products with ENFit Connectors: Implementation Timeline Delayed; SafetyShare; Jun. 18, 2015; 2 pgs.

* cited by examiner

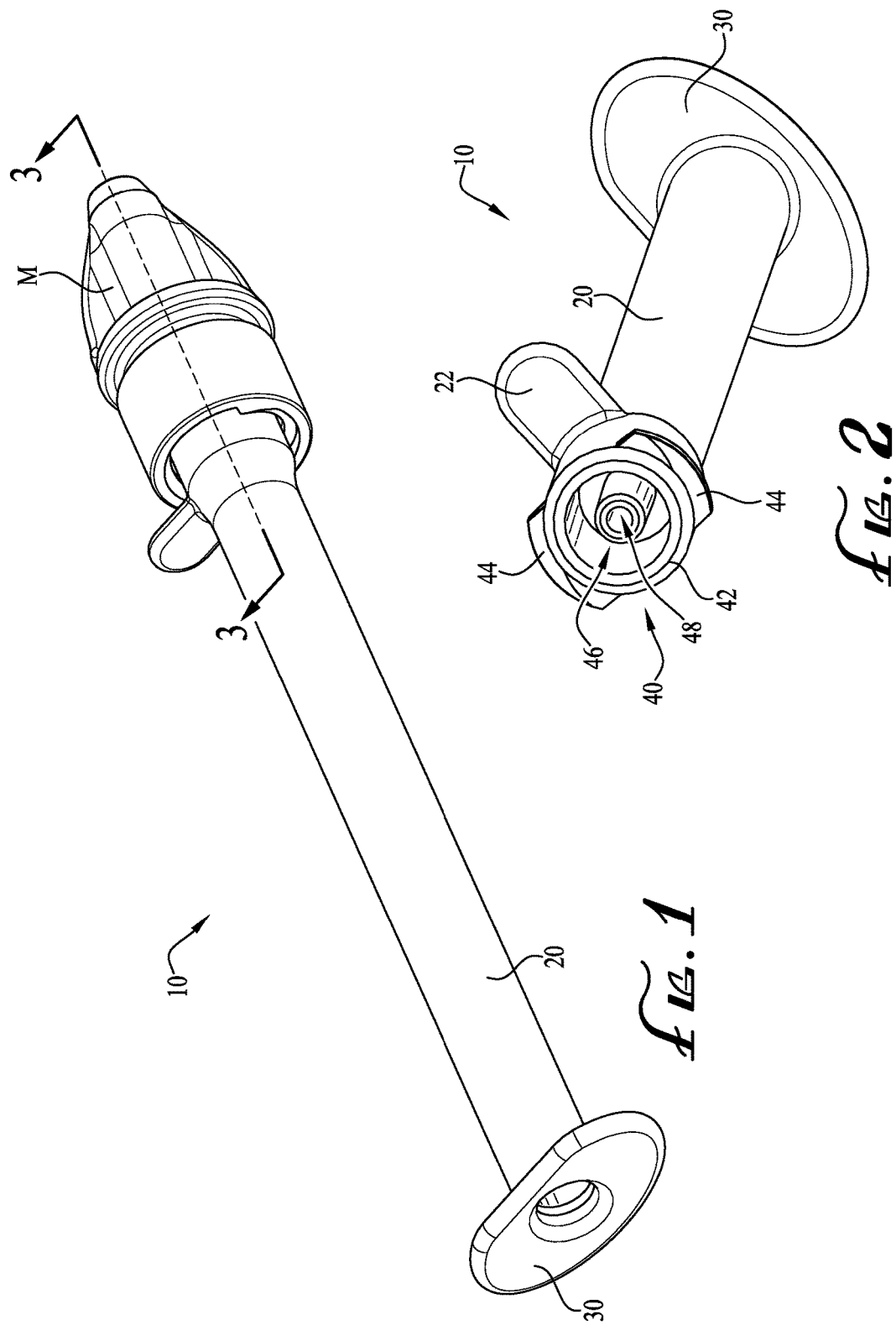

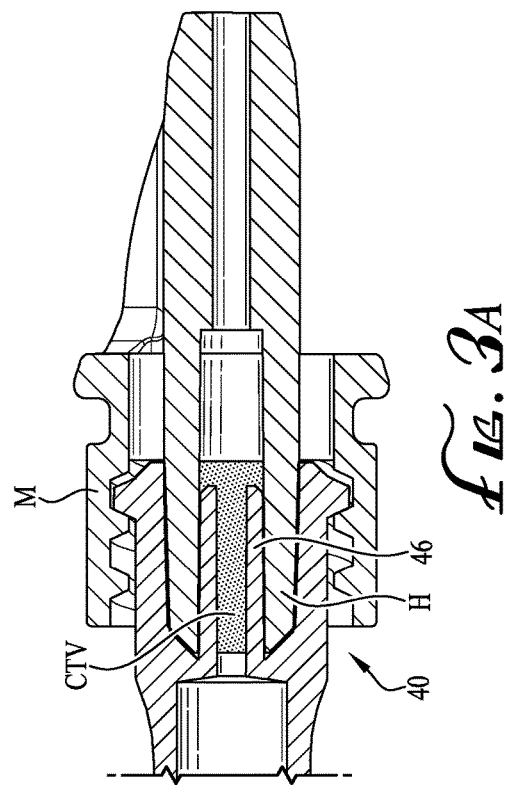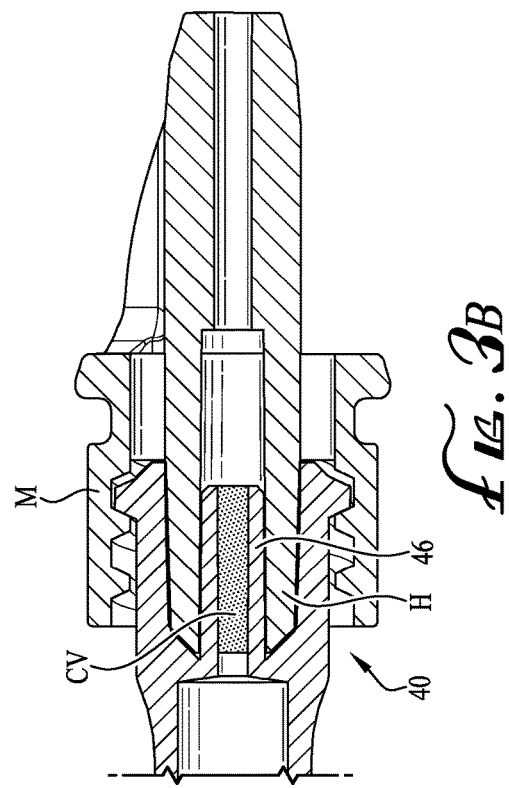

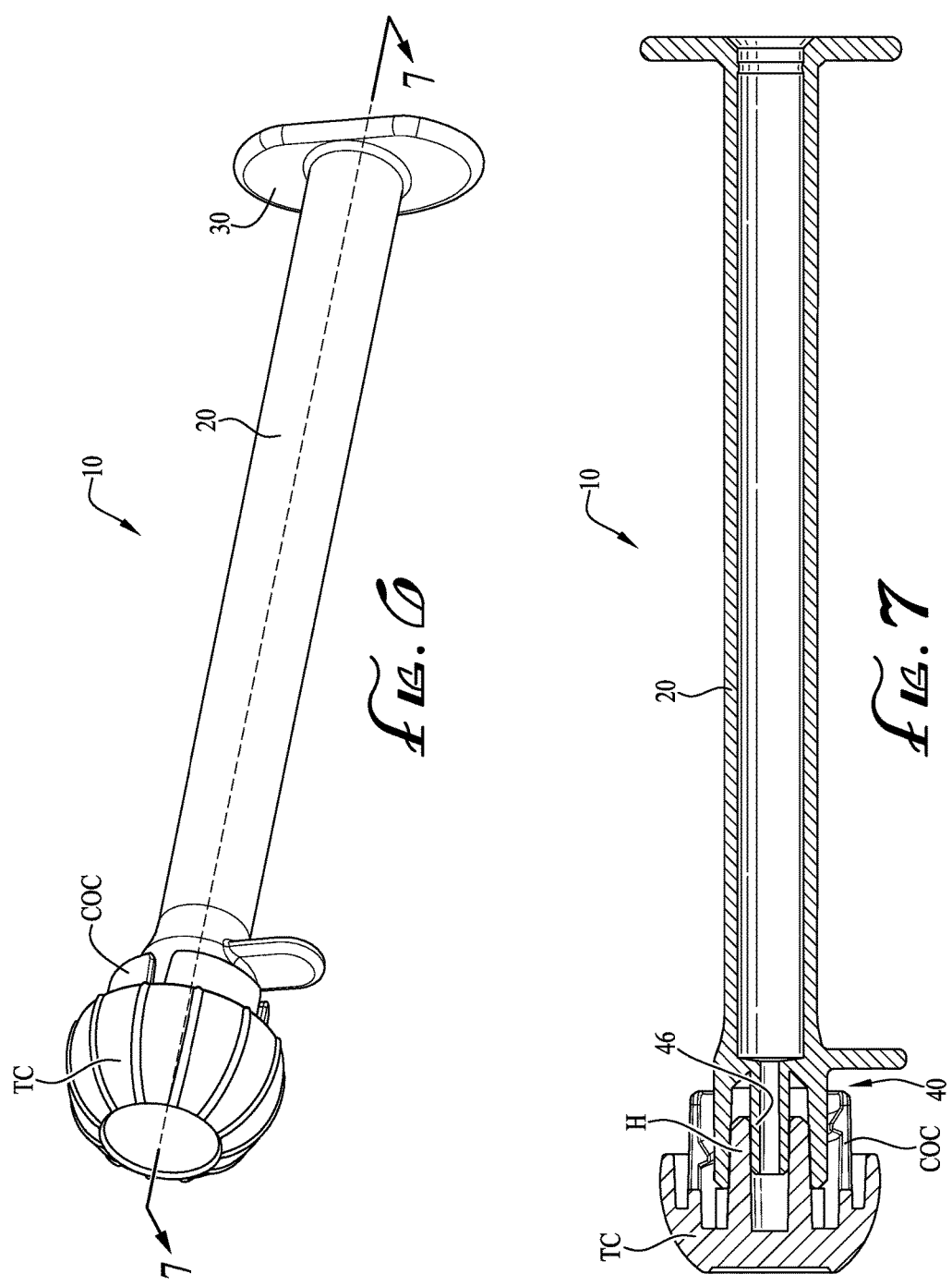

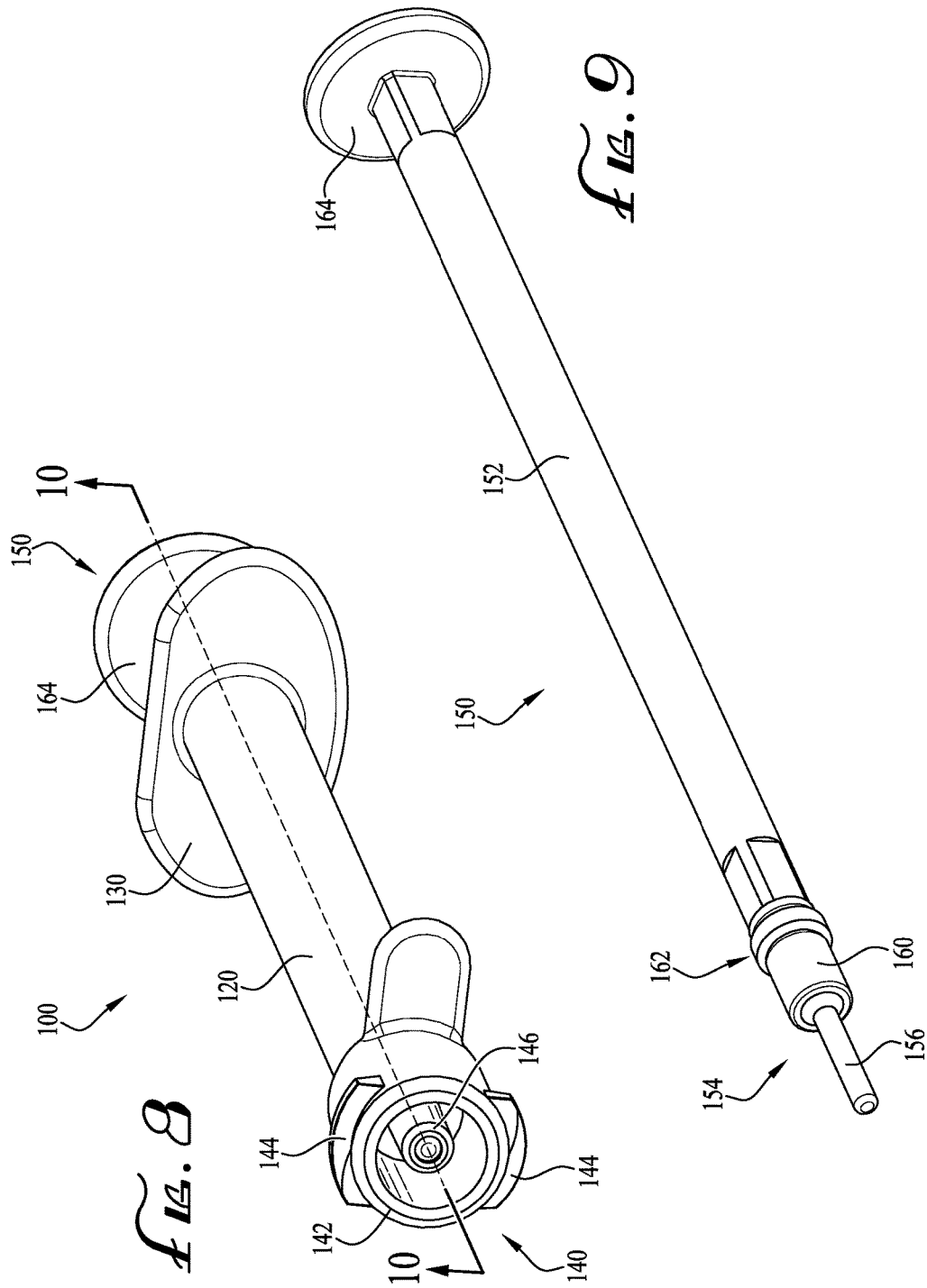

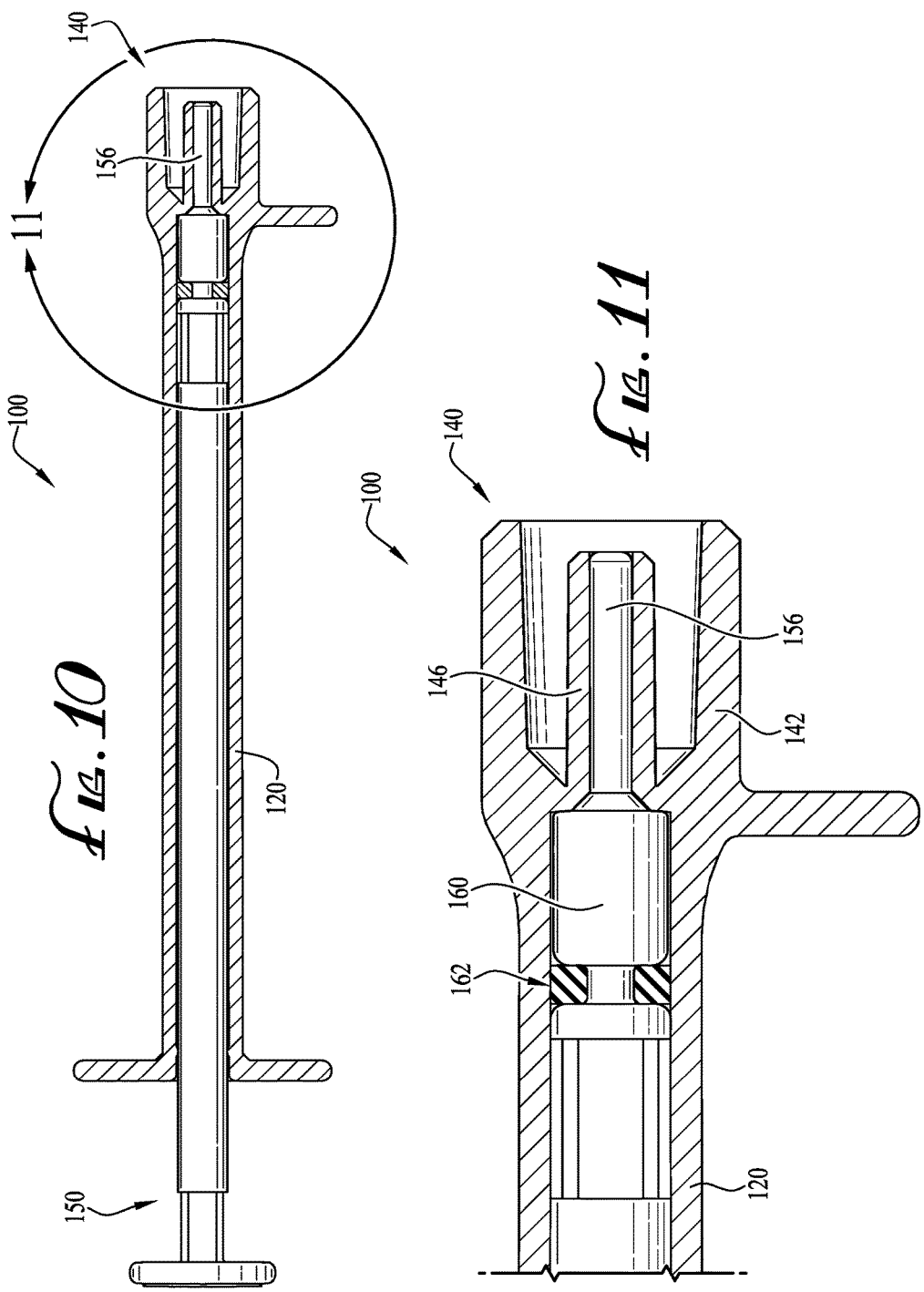

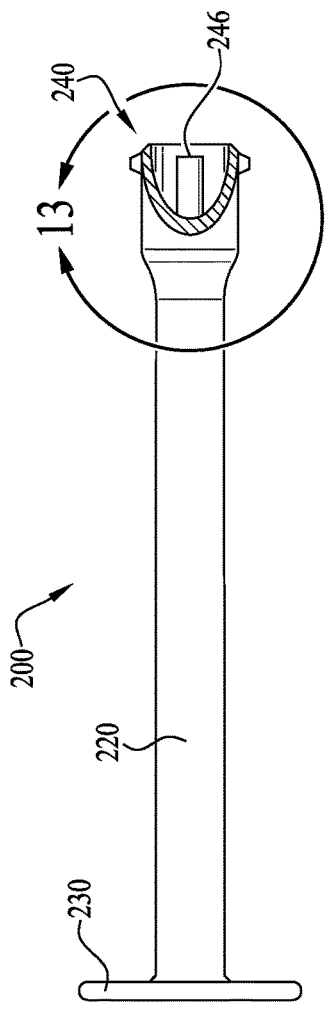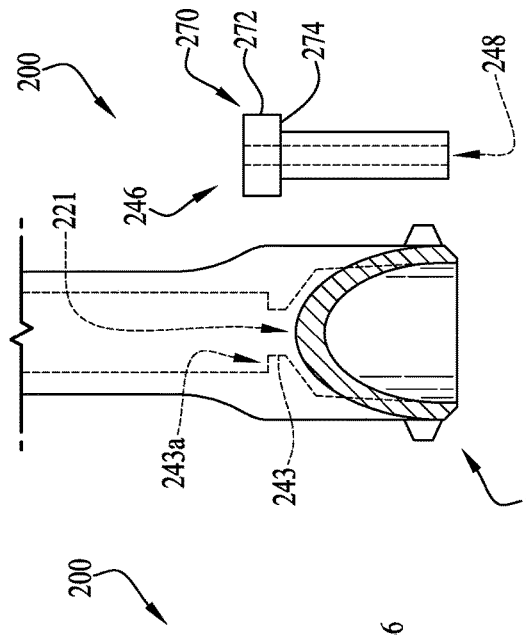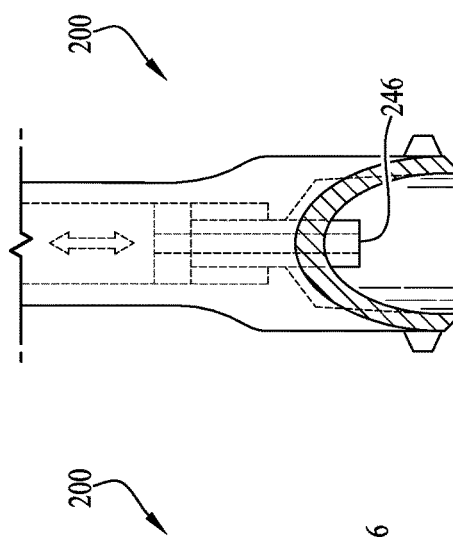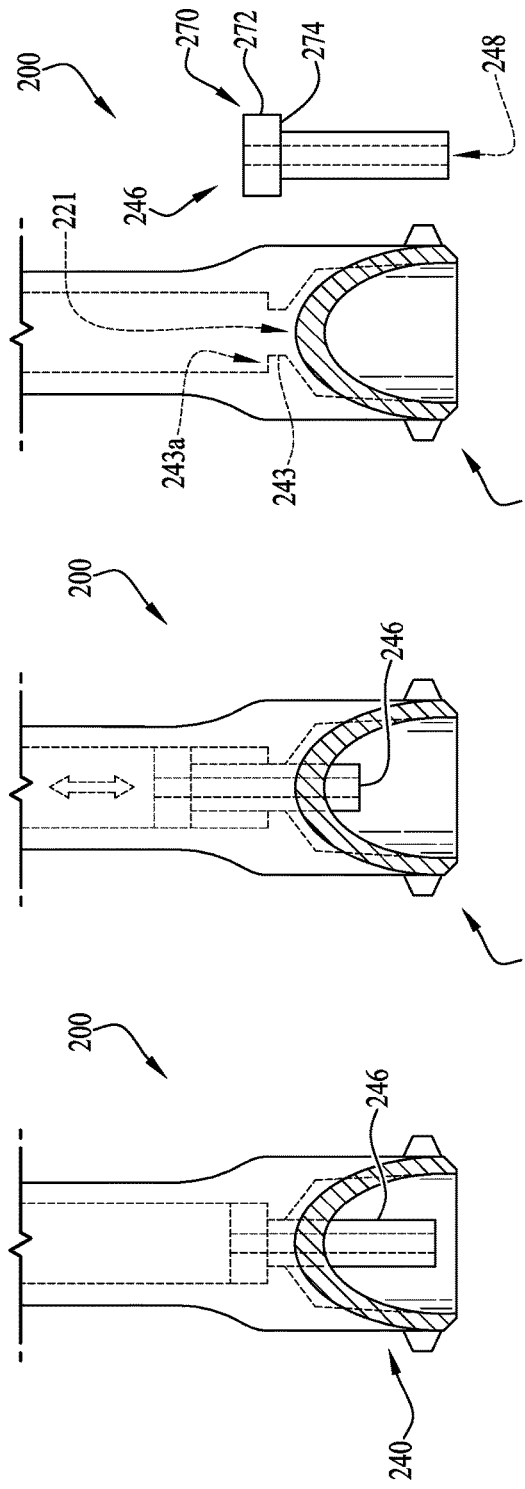

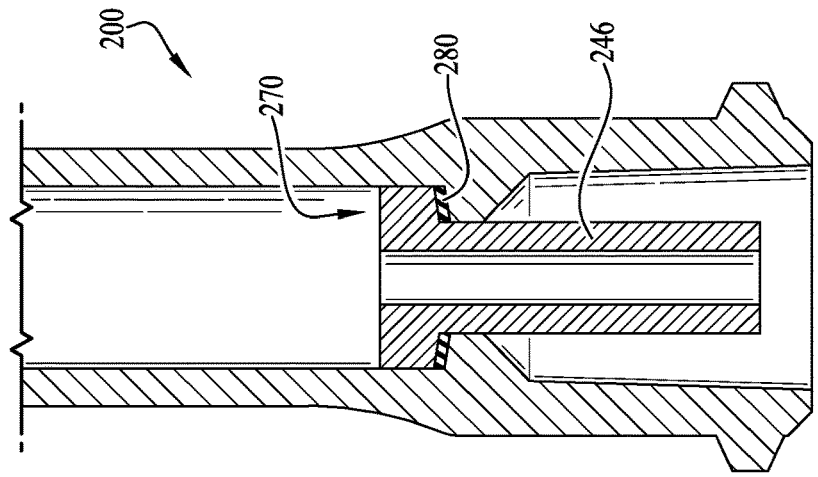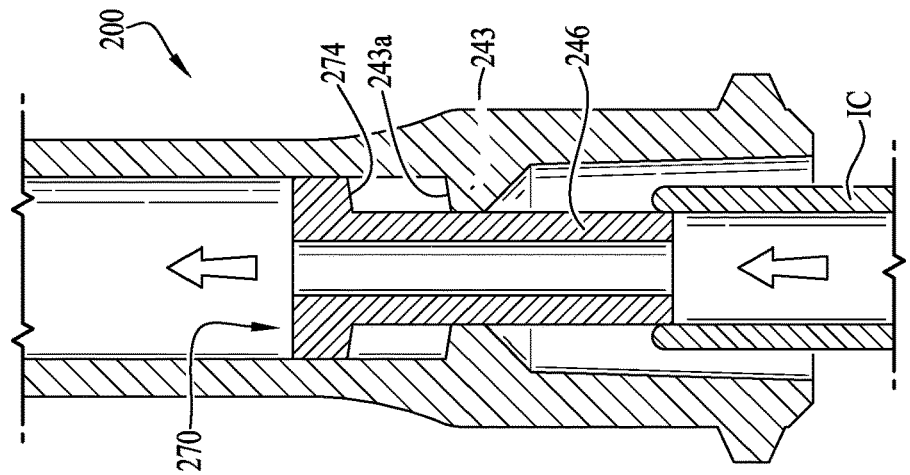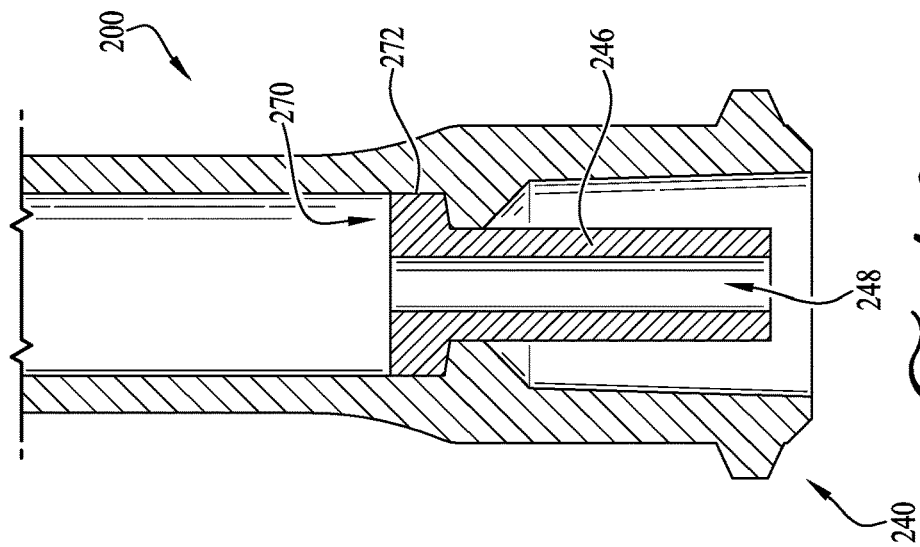

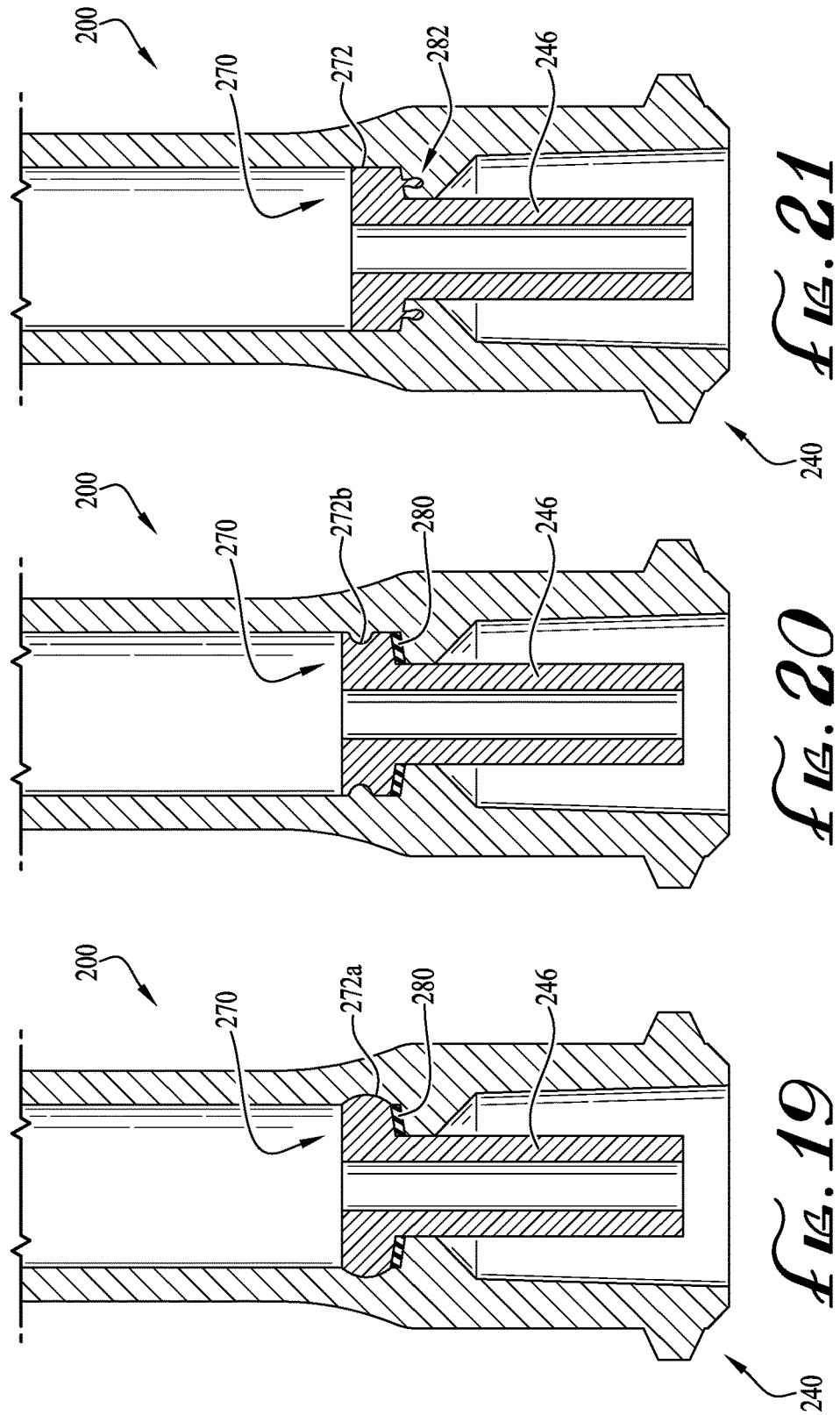

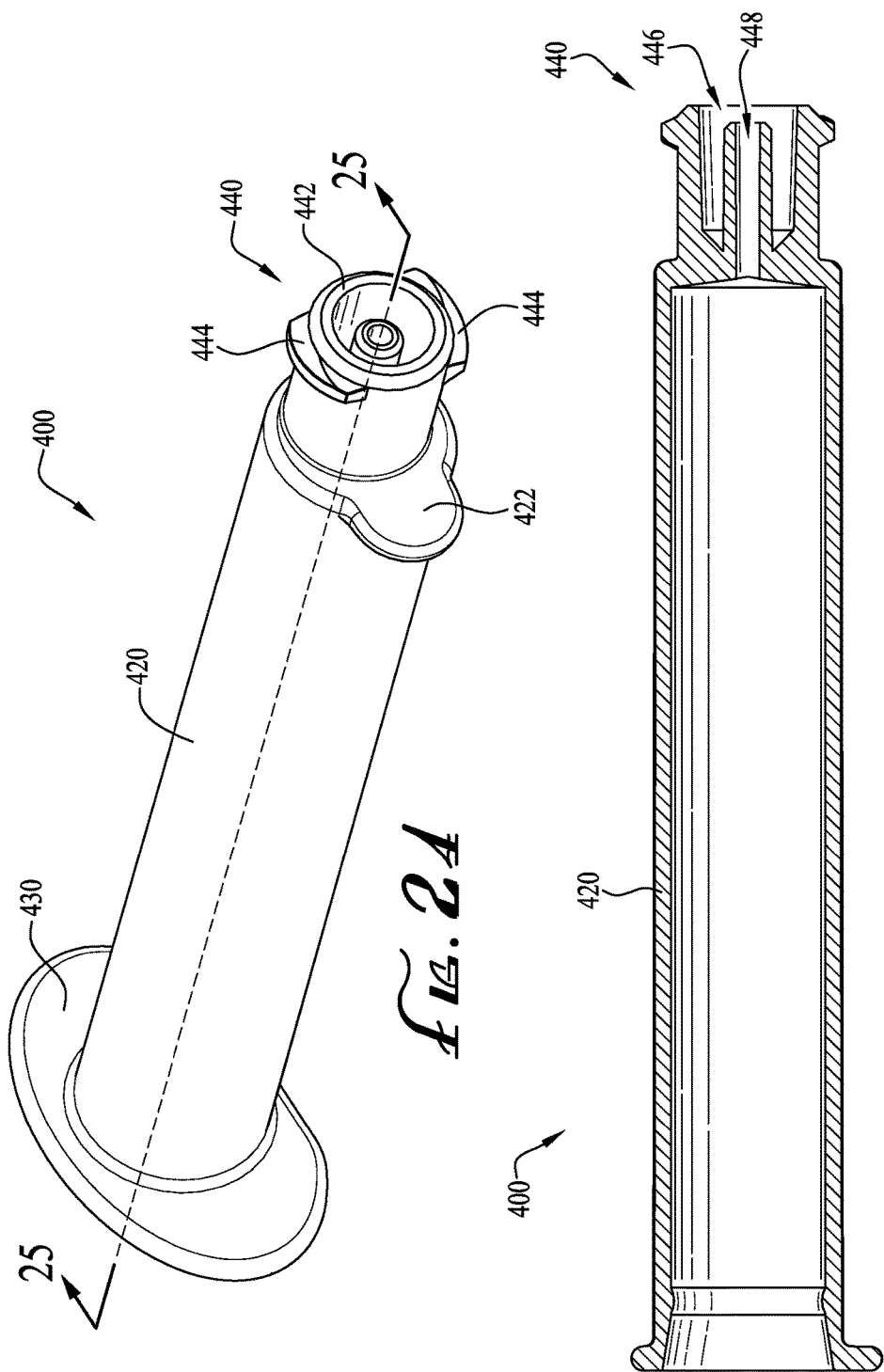

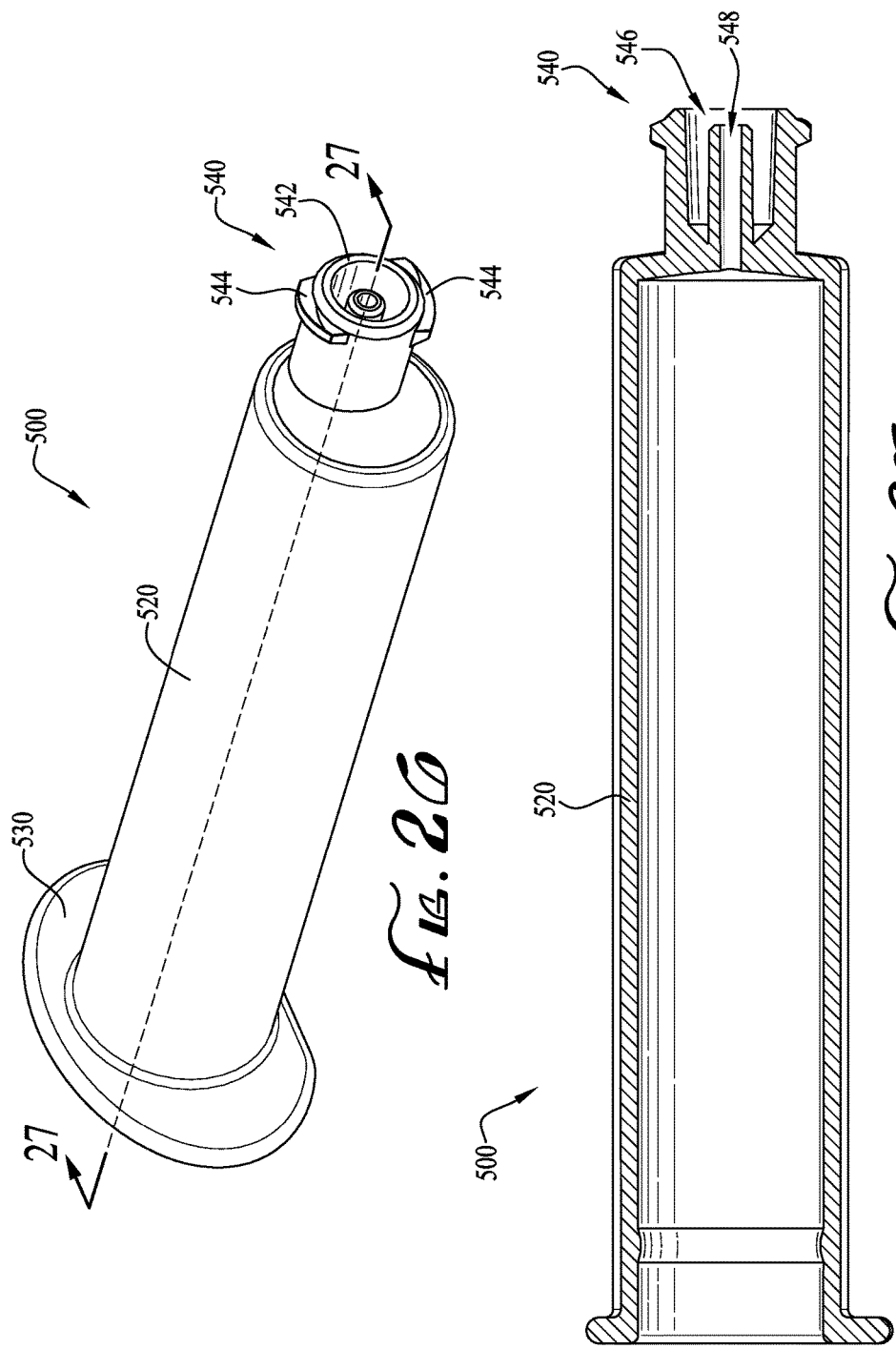

DOSING CONTROL COUPLING FOR ENTERAL FLUID TRANSFER

CROSS-REFERENCE TO RELATED APPLICATIONS

This application claims priority to U.S. Provisional Patent Application Ser. No. 62/350,934 filed Jun. 16, 2016, U.S. Provisional Patent Application Ser. No. 62/207,120 filed Aug. 19, 2015 and U.S. Provisional Patent Application Ser. No. 62/192,454 filed Jul. 14, 2015, all of which are hereby incorporated herein by reference in their entireties.

TECHNICAL FIELD

The present invention relates generally to the field of enteral feeding and fluid transfer devices, and more particularly to a coupling for an enteral syringe or other enteral fluid component, having a lumen extension tip for accurate control of dosing.

BACKGROUND

Healthcare patients and neonates are commonly administered fluids such as medication and nutrients through the use of enteral fluid delivery syringes and other enteral fluid transfer and delivery devices. Particularly in smaller volume quantities of enteral fluid delivery, accurate dosing measurement is often highly desirable. Commonly, variations in the size, configuration and positioning of cooperating coupling elements of enteral fluid delivery devices can result in dosing inaccuracies.

In particular, enteral syringes and other components having enteral-only couplings conforming to the new ISO 80369-3 design standard (commonly known as ENFit®) may have larger dimensions and thus larger contained volume or displacement within the coupling than previous enteral syringe designs. Volumetric differences in fluid delivery resulting from these changes may adversely affect accuracy of dosing in oral and/or enteral administration of fluids.

Thus it can be seen that needs exist for improved coupling configurations for enteral syringes and other components that enable more accurate control of fluid delivery dosing. It is to the provision of an improved enteral and/or oral dosing control coupling and enteral syringes and other equipment incorporating such dosing control couplings that the present invention is primarily directed.

SUMMARY

In example embodiments, the present invention provides an enteral dosing control coupling and enteral syringes and other equipment incorporating such dosing control couplings that enables more accurate control of fluid delivery dosing.

In example forms, the enteral dosing control coupling incorporates a modified female ISO 80369-3 compliant coupling having a lumen extension tip for engagement within the lumen of a male ISO 80369-3 compliant coupling. The lumen extension tip reduces the volume of residual fluid contained in the coupling, and retains a substantially consistent volume of residual fluid contained in the coupling during fluid transfer into and out of the enteral syringe. For example, a substantially consistent residual volume is contained in the lumen extension tip when a syringe incorporating such a dosing control coupling is coupled to a larger volume container for filling, and when the syringe is coupled to a feeding tube for fluid delivery. Furthermore, the syringe incorporating the dosing control coupling can be coupled to other ENFit ISO 80369-3 compatible couplings and connectors.

In one aspect, the present invention relates to an enteral dosing control coupling including a cylindrical collar defining a hollow internal chamber and a lumen extension tip projecting axially into the internal chamber. An internal lumen extends axially through the lumen extension tip. In example embodiments, external coupling members are formed on a portion of the cylindrical collar.

In another aspect, the present invention relates to an enteral syringe including a hollow cylindrical barrel and a dosing control coupling. The hollow cylindrical barrel includes a cylindrical collar with an internal chamber and external coupling members. The dosing control coupling includes a lumen extension tip projecting axially into the internal chamber, and defining an internal lumen extending therethrough. In example embodiments, the cylindrical collar is generally shaped and sized according to the ISO 80369-3 standard. In one example form, the lumen extension tip is generally integrally formed with the cylindrical collar. In another example form, the lumen extension tip is a separate piece and configured to provide for removable coupling engagement with a portion of the enteral syringe.

In example forms, the lumen extension tip includes a generally elongate cylindrical body having a base portion for coupling engagement within the hollow cylindrical barrel of the enteral syringe. The base portion includes an outer peripheral surface for engagement with a surface defined by the hollow cylindrical barrel. In some example forms, the lumen extension tip comprises a sealing member for providing a seal between the hollow cylindrical barrel and the base portion of the lumen extension tip. In example forms, the outer peripheral surface of the base portion includes one or more engagement features for cooperating engagement with an engagement feature provided within the hollow cylindrical barrel.

In some example forms, a plunger is axially movable within the barrel to fill and dispense fluid into and from the syringe. The plunger optionally includes an elongate body having a forward end with a spear-like tip that is insertable within the internal lumen of the lumen extension tip of the syringe such that a contained volume within the internal lumen of the lumen extension tip is substantially zero. In this way, dosing inconsistencies and anomalies in accuracy during fluid delivery are substantially, if not entirely, eliminated.

In yet another aspect, the present invention relates to a lumen extension tip for use with an enteral syringe and for compatible fitting engagement within an internal conduit of a hub of a male ISO 80369-3 compliant coupling. The lumen extension tip includes an elongate cylindrical body, an internal conduit extending entirely through the cylindrical body, and a base portion including an outer peripheral surface and an abutment surface. The outer peripheral surface is configured for engagement with a hollow cylindrical barrel of the enteral syringe and the abutment surface is configured for seating engagement with an upper surface of a platform defined within the hollow cylindrical barrel. In example forms, a sealing member is provided and positioned between the abutment surface and the upper surface of the platform. In example embodiments, the outer peripheral surface of the base portion and an inner surface of the hollow cylindrical barrel can be shaped and sized to provide for removable engagement therebetween These and other aspects, features and advantages of example embodiments of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of embodiments of the invention, and are not restrictive of the invention, as claimed.

BRIEF DESCRIPTION OF THE DRAWINGS

FIG. 1 is a perspective view of an enteral syringe barrel including an enteral dosing control coupling according to an example embodiment of the present invention, shown connected to a male ISO 80369-3 compliant coupling.

FIG. 2 is a second perspective view of the enteral syringe of FIG. 1, disconnected from the male ISO 80369-3 compliant coupling, and showing the proximal end incorporating a lumen extension tip.

FIGS. 3A-B show cross-sectional views of an enteral dosing control coupling according to the present invention, connected to a male ISO 80369-3 compliant coupling, showing the small variation of residual volume contained in the lumen extension tip.

FIG. 6 shows the enteral syringe of FIG. 1, with a tip cap closure mounted on its proximal end.

FIG. 7 shows a cross-sectional view of the enteral syringe and mounted tip cap enclosure of FIG. 6 taken along line 7-7.

FIG. 8 is a perspective view of an enteral syringe including a hollow cylindrical barrel, an enteral dosing control coupling, and a plunger movably mounted within the barrel, according to another example embodiment of the present invention.

FIG. 9 is a perspective view of the plunger of FIG. 8, removed from the syringe barrel.

FIG. 10 is a cross sectional view of the enteral syringe of FIG. 8.

FIG. 11 is a detailed cross-sectional view of the enteral dosing control coupling portion of the syringe of FIG. 10.

FIG. 12 shows an enteral syringe including an enteral dosing control coupling in the form of a lumen extension tip according to another example embodiment of the present invention, and showing a section of the coupling removed to show internal portions thereof.

FIG. 13 shows a detailed view of the enteral syringe of FIG. 12, and showing the lumen extension tip of the enteral dosing control coupling in a seated and fully extended position.

FIG. 14 shows a detailed view of the enteral dosing control coupling of FIG. 12, and showing the lumen extension tip of the enteral dosing control coupling at least partially retracted within the syringe.

FIG. 15 shows a detailed view of the enteral dosing control coupling of FIG. 12, and showing the lumen extension tip of the enteral dosing control coupling entirely removed from the syringe.

FIG. 16 shows a cross-sectional view of the enteral syringe of FIG. 12.

FIG. 17 shows the lumen extension tip of FIG. 12 retracted within the syringe by misconnecting a non-ENFit enteral connector with the lumen extension tip.

FIG. 18 shows a cross-sectional view of an enteral syringe with the lumen extension tip thereof having a sealing member according to another example embodiment of the present invention.

FIG. 19 shows a cross-sectional view of an enteral syringe with the lumen extension tip thereof having a sealing member and interengagement features according to another example embodiment of the present invention.

FIG. 20 shows a cross-sectional view of an enteral syringe with the lumen extension tip thereof having a sealing member and interengagement features according to another example embodiment of the present invention.

FIG. 21 shows a cross-sectional view of an enteral syringe with the lumen extension tip thereof having interengagement features according to another example embodiment of the present invention.

FIG. 24 is a perspective view of a syringe having a dosing control coupling according to another example embodiment of the present invention.

FIG. 25 shows a cross-sectional view of the syringe of FIG. 24 taken along line 25-25.

FIG. 26 is a perspective view of a syringe having a dosing control coupling according to another example embodiment of the present invention.

FIG. 27 shows a cross-sectional view of the syringe of FIG. 24 taken along line 27-27.

DETAILED DESCRIPTION OF EXAMPLE EMBODIMENTS

Figure 4:
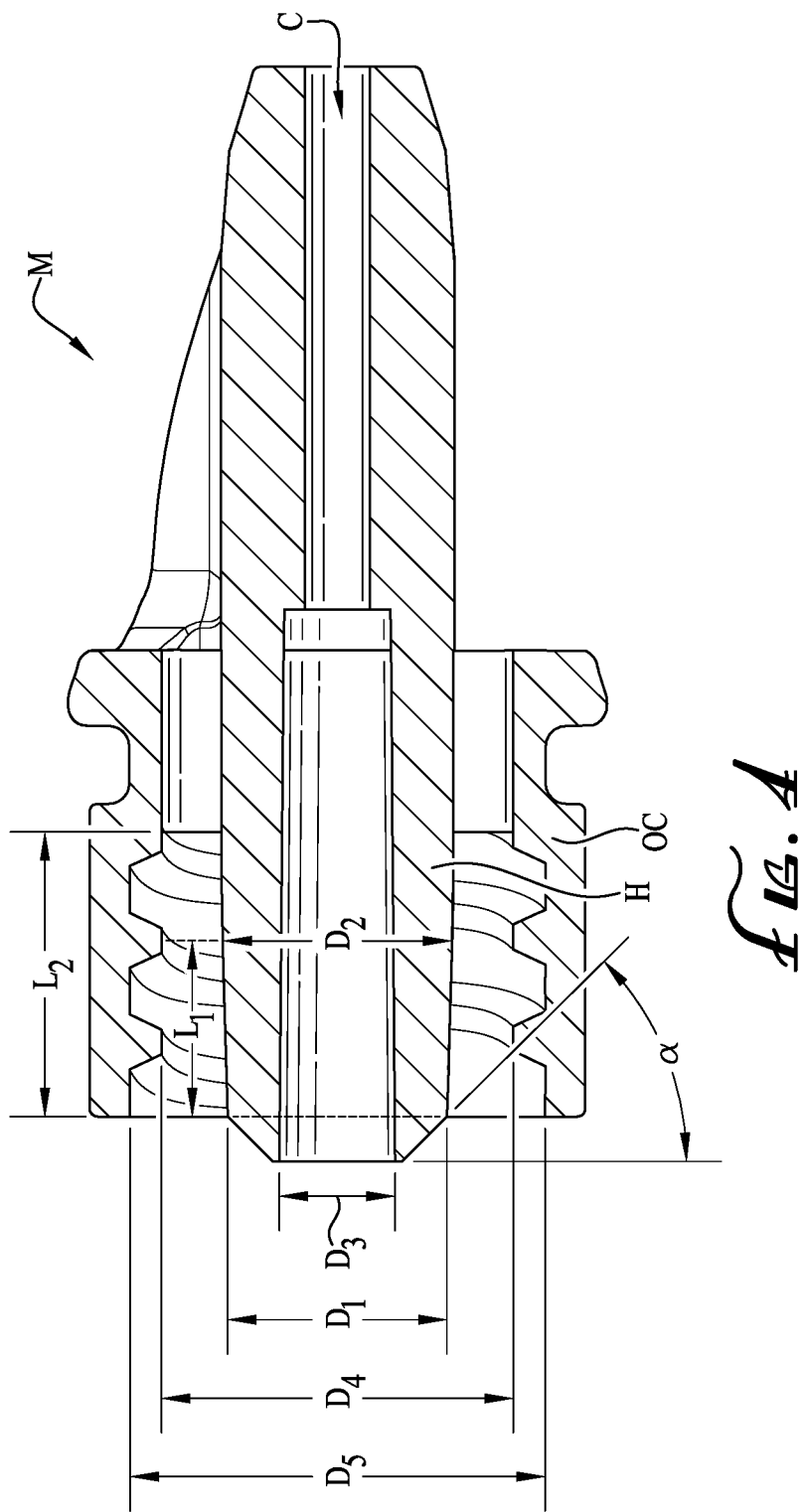
FIG. 4 shows a cross-sectional view of the male ISO 80369-3 compliant coupling of FIGS. 3A-B.

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-7 show an enteral syringe 10 comprising an enteral dosing control coupling or low-dose tip according to an example form of the invention. In example forms, the enteral syringe 10 includes a hollow cylindrical barrel 20, a base flange 30 at a distal end of the barrel, and an enteral dosing control coupling 40 at a proximal end of the barrel. As would be understood by one of ordinary skill in the art, the barrel 20 is adapted to receive a syringe plunger (see FIG. 8, as will be described below), which is axially advanced and retracted within the barrel to fill and dispense fluid into and from the syringe in typical fashion. A positioning flange 22 optionally extends transversely outward from the barrel 20, proximal the coupling 40. In some example embodiments, the syringe can be provided for use with a syringe pump, for example, where one or more portions of the syringe and/or the plunger can be interengageable with one or more portions of the syringe pump for moving the plunger relative to the syringe to dispense fluids from the syringe.

Figure 5:
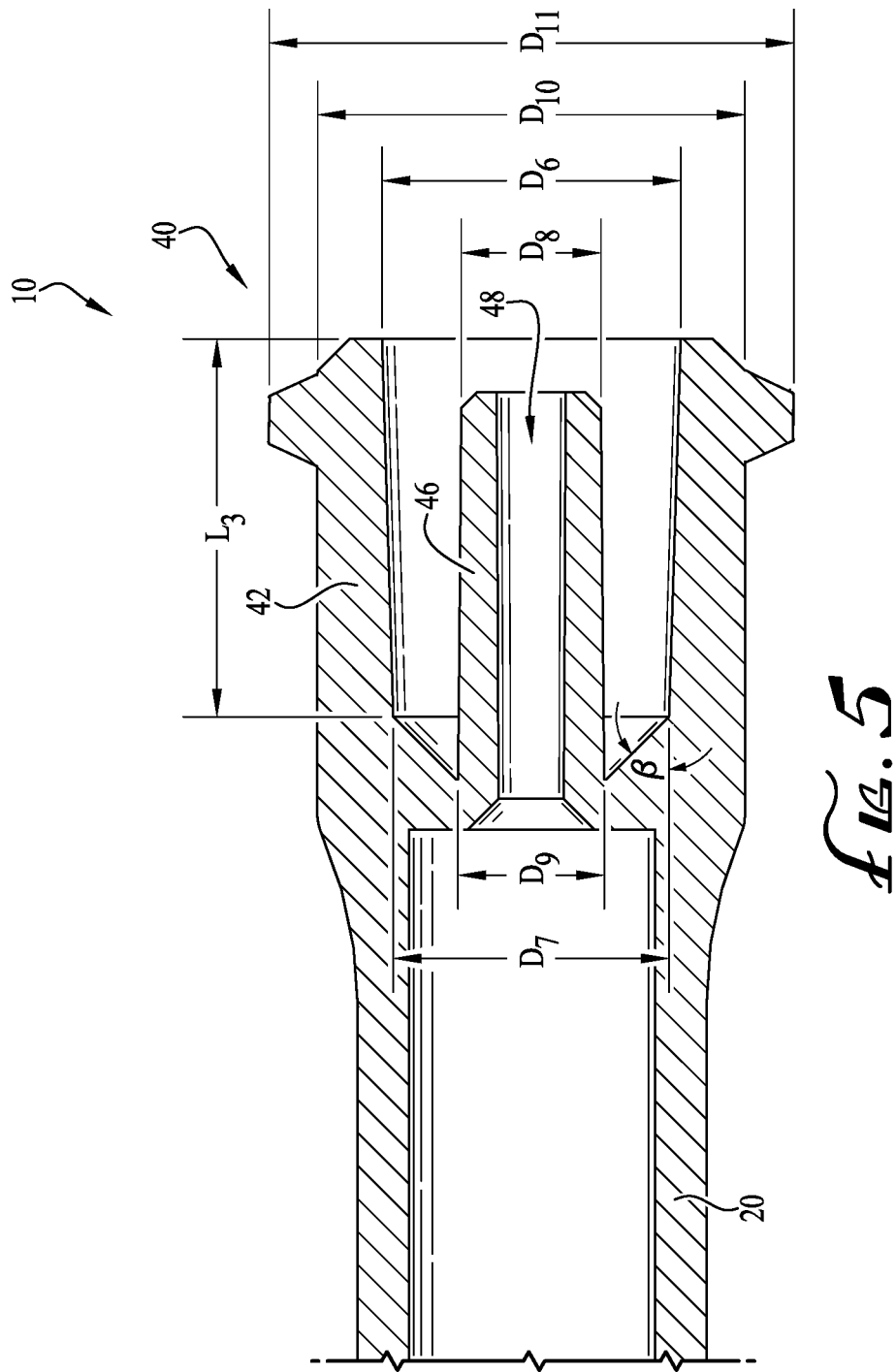
FIG. 5 shows a cross-sectional view of the female ISO 80369-3 compliant coupling portion of the enteral syringe of FIGS. 3A-B.

In the depicted example embodiment, the coupling 40 generally comprises a modified female ENFit coupling substantially conforming to ISO design standard 80369-3, and is engageable with a compatible coupling element such as a corresponding male ISO 80369-3 compliant coupling M, as shown in FIG. 1. In example applications, the male ISO 80369-3 compliant coupling M can be part of a feeding or extension tube, a pharmacy cap, or other enteral fluid delivery equipment to which the syringe 10 is to be coupled. As depicted in FIGS. 2 and 5, the coupling 40 comprises a cylindrical outer collar 42 defining a hollow internal chamber, and a pair of helical coupling lugs 44 projecting outwardly from the exterior surface of the collar. Optionally, rather than lugs 44 projecting from the exterior surface of the collar, the exterior surface of the collar 42 can comprise helical threads generally extending about at least a portion of the exterior surface thereof, for example, like threads on a bolt, other types of conventional coupling members, etc. In some example embodiments, the exterior surface of the collar is entirely smooth without any lugs, for example, whereby a frictional fit (as will be described below) will be provided between the male ISO 80369-3 compliant coupling M and the coupling 40.

The coupling 40 further comprises a lumen extension tip 46, projecting axially from the barrel 20 of the syringe into the internal chamber of the collar 42. An internal lumen or enteral fluid delivery conduit 48 extends through the lumen extension tip 46 for fluid communication to and from the contained volume of the barrel 20, allowing fluid delivery in and out of the barrel. As shown in cross-section by FIGS. 3A-B, when the coupling 40 is engaged with a male ISO 80369-3 compliant coupling M, the lumen extension tip 46 is received within the lumen of a male coupling hub H (in effect becoming a male coupling element within the "female" lumen of the male ISO 80369-3 compliant coupling). The lumen extension tip 46 is generally cylindrical or tubular and includes an internal surface defining the lumen or fluid delivery conduit 48, a cylindrical or slightly tapered external surface, and a distal tip at its free end. The outer coupling collar 42 is also generally cylindrical or tubular, and at least partially surrounding the lumen extension tip 46. The collar 42 comprises an internal surface confronting and spaced a distance apart from the external surface of the lumen extension tip, and further comprises an external surface optionally comprising the lugs 44 or other coupling or connection features, and an outer rim at its distal free end. The internal dimension of the collar 42 is greater than the external dimension of the lumen extension tip 46, such that a space therebetween forms a receiver for a cooperating portion of a compatible coupling element. The lumen extension tip 46 is positioned generally concentrically and coaxially within the collar 42, and the lumen 48 extends generally centrally through the lumen extension tip also concentric and coaxial with the collar.

According to example forms, the lumen extension tip 46 is integrally formed with the coupling 40 whereby an internal end surface of the barrel 20 provides support for the extension of the tip 46 within the internal chamber of the collar 42. Typically, the lumen extension tip 46 is generally sized and shaped for substantially fitting within the lumen of the male coupling hub H of the male ISO 80369-3 compliant coupling M (see FIGS. 3A-B). In example embodiments, the coupling 40 (comprising the lumen extension tip 46) is preferably engagable with both compliant and other compatible ISO 80369-3 connectors. In some example embodiments, the extension of the tip 46 does not extend beyond an end of the collar 42, for example, such that the tip is recessed between about 0.45-0.65 millimeters below the end of the collar 42, for example about 0.55 millimeters according to example embodiments. However, according to other example forms, the tip 46 extends beyond the end of the collar 42. In example forms, the size, shape and extension of the tip 46 is generally configured for compatible engagement within the lumen of the male coupling hub H.

In example embodiments, the lumen extension tip 46 is configured such that dosing inconsistencies and anomalies in accuracy during fluid delivery are reduced, minimized or substantially eliminated. With respect to the coupling configuration shown in FIGS. 3A-B, it can be seen that the lumen extension tip 46 retains a substantially consistent volume of residual fluid contained in the internal lumen 48 of the extension tip during fluid transfer into and out of the enteral syringe. In example embodiments, the contained volume CV of the lumen extension tip 46 is between about 0.005 milliliters to about 0.03 milliliters, and more preferably about 0.01 milliliters (see FIG. 3B). In example embodiments the combined tip volume CTV (e.g., lumen plus the rest of the fluid space in the tip) is preferably about 0.017 milliliters (see FIG. 3A).

As depicted in FIG. 4 and as described above, the male coupling M is preferably compatible with the ISO 80369-3 standard. For example, the male coupling hub H comprises a first outer diameter D1 that is defined at an end of the hub H adjacent the beginning of a tapered end surface (defined by angle α), a second outer diameter D2 that is defined at a length L1 from the end of the hub H adjacent the taper. The internal lumen of the hub H is defined by a diameter D3. An outer collar OC generally surrounds the hub H for providing coupling engagement with the lugs 44 of the coupling 40 of the syringe 10. The outer collar comprises a minor inside thread diameter D4 and a major inside thread diameter D5. The length of the hub H from the end of the outer collar OC is defined by a length L2. In typical configurations, the first outer diameter D1 is about 5.41 millimeters, the second outer diameter D2 is about 5.64 millimeters, the internal lumen diameter D3 is about 2.90 millimeters, the minor inside thread diameter D4 is about 8.65 millimeters, the major inside thread diameter D5 is about 10.23 millimeters, and the angle α is about 45 degrees. In some configurations, the diameter D5 is larger than 10.23 millimeters, for example, wherein the male hub H generally relies on frictional engagement with the coupling 40 (e.g., instead of the lugs 44 engaging the threads of the outer collar OC). Alternatively, the collar 42 can be substantially without lugs such that the outer collar 42 can generally pass between the first and second diameters D1, D2 of the hub H and the minor inside thread diameter D4, for example, where a frictional fit is provided between the hub H and an interior or inner wall of the collar 42. The length L1 is about 3.82 millimeters and the length L2 is about 6.82 millimeters or greater.

In example embodiments, the coupling 40 (and enteral dosing control coupling thereof) is compatible with the ISO 80369-3 standard, for example, to provide for coupling engagement with the male coupling M (and the hub H thereof). For example, as depicted in FIG. 5, the coupling 40 comprises a first internal diameter D6 and a second internal diameter D7 that are spaced a length L3 between each other. The lumen extension tip 46 comprises a first outer diameter D8 defined near its end and a second outer diameter D9 defined at the connected side of the tip 46. An angled taper (defined by an angle β) is provided between the base end of the tip 46 and an internal surface of the collar 42. The lugs 44 of the collar 42 define a minor outside thread diameter D10 and a major outside thread diameter D11. According to example embodiments, the first internal diameter D6 is about 5.69 millimeters, the second internal diameter D7 is about 5.26 millimeters, the first outer diameter D8 of the tip 46 is about 2.50 millimeters, the second outer diameter D9 of the tip 46 is about 2.85 millimeters, the minor outside thread diameter D10 is about 8.10 millimeters, and the major outside thread diameter D11 is about 9.93 millimeters. The length L3 defined between the first and second internal diameters D6, D7 is about 7.14 millimeters, and the angle β of the angled taper is about 45 degrees. Optionally, according to alternate example forms, the male coupling M and the coupling 40 can be sized as desired.

In example embodiments, the first and second outer diameters D8, D9 of the lumen extension tip 46 are generally sized and shaped to provide for compatible fitting engagement within the internal lumen of the hub H of the male coupling M (defined by internal diameter D3). Thus, with the internal lumen diameter D3 being about 2.90 millimeters, the first and second outer diameters D8, D9 are preferably sized to provide for fitting engagement within the internal lumen thereof. In some example forms, the first and second diameters D8, D9 are configured such that little to no interference is provided between the tip 46 and the internal lumen of the hub H. Alternatively, the first and second diameters D8, D9 can be configured such that at least some interference is provided therebetween to frictionally and/or sealingly engage the two together.

In example embodiments, the lumen extension tip 46 preferably assists in the prevention of unwanted fluid transfer when uncoupling the coupling hub H from the syringe 10. Typically, a vaccuum is formed when the coupling hub H and the syringe 10 are coupled together and fluid is communicating therebetween (or stagnant therein). Thus, by providing the lumen extension tip 46, a smaller quantity of fluid is present and subject to being transferred back into the syringe 10. Accordingly, provision of the lumen extension tip 46 preferably minimizes the unwanted transfer of fluid, which is intended to be carried within and out of the coupling hub H, from being drawn back into the syringe 10 when the connection between the coupling hub H and the lumen extension tip 46 is broken.

While the coupling 40 comprising the lumen extension tip 46 is described and shown herein as part of an enteral syringe, it will be understood that the lumen extension tip of the present invention may be incorporated in the coupling elements of various other types of enteral fluid collection, storage and/or transfer devices as well. Thus, the present invention includes without limitation, a coupling (such as for example, a modified female ISO 80369-3 compliant coupling) including a lumen extension tip as disclosed, as well as enteral fluid collection, storage and/or transfer devices comprising such a coupling, for example, syringes of differing sizes and formats, enteral fluid collection devices, enteral fluid storage devices, enteral fluid delivery or transfer tubes or conduits, enteral connectors or couplings, and the like, as well as accessories, couplings and adaptors for use in connection with various ISO 80369-3 compliant or non-ENFit enteral fluid storage and delivery devices.

For example, according to one example embodiment as depicted in FIGS. 6-7, a tip cap TC can be coupled to the coupling 40 for sealing the internal lumen 48 to prevent fluids from dispensing from the internal lumen, and for preventing debris and contaminants from contacting the coupling 40 and internal lumen 48. According to one example embodiment, the tip cap TC comprises a male hub H (as described above) for providing interengagement with the coupling 40 (and for permitting extension of the lumen extension tip 46 within the internal cavity of the male hub H). According to one example embodiment, the tip cap TC comprises a coaxial connection collar that is modified to comprise a radial array of two or more split retainer tab members or clips COC, which are generally at least partially flexible and resilient for outwardly flexing during engagement with the lugs 44 of the coupling 40. U.S. patent application Ser. Nos. 15/078,674, 15/185,583, 14/844,922, 29/521,665, and 29/533,173 are incorporated herein by reference and disclose various clipped, snap-on and dual-action attachment and removal mechanisms. Optionally, one or more of the ends of the couplings can be provided with tabs or clips for providing permanent engagement between the coupling and the compatible connector, for example, when it is intended to prevent removal of the coupling 40 (and syringe 10 thereof) from the compatible connector after use.

In an example method of use, a syringe 10 is connected to another enteral fluid delivery component by engagement of the modified female ISO 80369-3 compliant coupling 40 of the syringe with a male ISO 80369-3 compliant coupling, in typical fashion. The lumen extension tip of the syringe coupling is received within the lumen of the male ISO 80369-3 compliant coupling. Fluid is transferred in or out of the syringe, from or to the other enteral fluid delivery component by retracting or advancing the syringe plunger. A reduced and substantially consistent residual volume is contained in the lumen extension tip during sequential fluid transfer operations, thereby maintaining accurate dosing control.

According to an example embodiment of the present invention, the plunger of the syringe is preferably configured such that an end thereof extends within the internal lumen 48 of the lumen extension tip 46 as the plunger is advanced into the syringe body for fluid delivery, for example, to eliminate the dead space within the internal lumen 48 of the lumen extension tip 46 so that dosing inconsistencies and anomalies in accuracy during fluid delivery are further reduced, minimized or substantially eliminated. As shown in FIGS. 8-9, for example, an enteral syringe 100 is shown and comprises a plunger 150 movably mounted within a hollow cylindrical barrel 120. In example forms, the plunger 150 comprises a generally elongate body 152 comprising a forward end portion 154 having a displacement member or generally spear-like tip or rod 156 at a forward end thereof. In the depicted embodiment, the forward end 154 includes a forward body portion 160, and a seal ring or gasket 162 positioned generally adjacent the forward end portion (see FIG. 9). Optionally, the rearward end of the plunger 150 can comprise an actuating flange or feature 164 for providing manipulation thereof to push or pull the plunger 150 into and out of the hollow cylindrical barrel 120.

FIGS. 10-11 show a cross-sectional view of the syringe 100 with the plunger 150 fully inserted within the hollow cylindrical barrel 120 and the tip 156 fully inserted within the internal lumen 148 of the lumen extension tip 146 of the modified ISO 80369-3 compliant coupling 140. Preferably, with the plunger 150 fully inserted therein, the contained volume within the internal lumen 148 of the lumen extension tip 146 is substantially zero, and thus, dosing inconsistencies and anomalies in accuracy during fluid delivery are substantially, if not entirely, eliminated. Typically, the size of the tip 156 is substantially similar to the size and shape of the internal lumen 148, and the size and shape of the elongate body 152 and forward end body portion 160 are substantially similar or slightly smaller than the size and shape of the hollow cylindrical barrel 120. According to example forms, the size of the gasket 162 is generally slightly greater than the size of the hollow cylindrical barrel 120.

FIGS. 12-17 show an enteral syringe 200 comprising an enteral dosing control coupling 240 according to another example form of the invention. As similarly recited above, the enteral syringe 200 includes a hollow cylindrical barrel 220, a base flange 230 at a distal end of the barrel, and the enteral dosing control coupling 240 at a proximal end of the barrel. The barrel 220 is adapted to receive a syringe plunger, which is axially advanced and retracted within the barrel to fill and dispense fluid into and from the syringe in typical fashion. In example forms, a lumen extension tip 246 is generally floating or movable with respect to the syringe (e.g., a separate piece), and is generally fitted and interengageable within the barrel of the syringe such that at least a portion thereof extends from the coupling 240 (as similarly described above). According to example embodiments, configuring the lumen extension tip as a separate piece further de-risks the chances of a misconnection with a non-ENFit connector, and a substantially wide variety of options are available regarding the manufacturing and assembly of the tip and the syringe.

The lumen extension tip 246 comprises an internal lumen 248, and functions substantially similarly to the embodiments as described above, for example, such that dosing control inaccuracies are substantially eliminated to provide for accurate dosing control. As depicted in FIGS. 12-15, a portion of the coupling 240 is removed to show internal portions thereof. However, according to some example embodiments, the coupling 240 can comprise one or more cut-outs or removed sections (e.g., as depicted) to facilitate the removal and evacuation of any fluids that are contained within the coupling 240, for example, within the area defined between the lumen extension tip 246 and an interior wall portion of the coupling 240. In some example forms, about one cut-out portion is formed within the coupling 240. In other example embodiments, two or more cutouts are formed within the coupling 240. According to some example forms, one or more openings can be formed along any portion of the coupling 240, for example, to act as a drain or exit conduit for facilitating the removal of unwanted fluids.

As depicted in FIGS. 13 and 16, the lumen extension tip 246 is preferably configured for fitting within at least a portion of the barrel 220, for example, such that at least a portion of the tip 246 extends coaxially within at least a portion of coupling 240, or within at least a portion of the space defined and surrounded by the collar of the modified female ISO 80369-3 compliant coupling substantially conforming to ISO design standard 80369-3, and is engageable with a corresponding male ISO 80369-3 compliant coupling M, as shown in FIG. 1. As depicted in FIG. 15, the lumen extension tip 246 generally comprises a cylindrical body defining the conduit 248 extending therethrough. In example forms, an end of the cylindrical body comprises a base portion 270 having an outer peripheral surface 272 for being retained within the internal conduit of the barrel. Furthermore, a contact or abutment surface 274 is provided for engaging a portion of the internal conduit within the barrel 220 (e.g., to define an in-use, fully-extended position). For example, as shown in FIGS. 15 and 17, an end of the internal conduit within the barrel 220 comprises an outer shelf or inwardly directed platform 243 defining an upper surface 243a for contact with the abutment surface 274 of the lumen extension tip 246, and wherein a centrally-positioned opening or conduit 221 is defined for receiving the cylindrical body of the lumen extension tip 246. In example embodiments, the outer peripheral surface 272 is generally similar in diameter and generally parallel with at least a portion of the internal conduit of the syringe barrel 220. In example forms, a frictional fit is provided between the outer wall of the internal conduit of the barrel 220 and the outer peripheral surface 272 of the base portion 270, or at least when the abutment surface 274 is contacting the upper surface 243a of the platform 243. For example, to ensure fluids do not pass around the outer peripheral surface 272 and through the conduit 221 of the syringe coupling 240 (e.g., leaking from the coupling and not being contained within the internal lumen 248), an interference fit is generally provided between the at least a portion of the base 270 and the platform 243.

In some example forms, as depicted in FIG. 18, a seal ring or gasket 280 is generally provided for seating against the abutment surface 274 and around the cylindrical body 246, and thereby providing for an enhanced seal between the upper surface 243a and the abutment surface 274. In example forms, when the gasket 280 is provided, the outer diameter of the outer peripheral surface 272 need not be the exact same size or larger for providing an interference fit. However, in some example forms, the outer diameter of the outer peripheral surface 272 is generally substantially similar to the diameter of the internal conduit of the barrel 220 generally near the platform 243, for example, to provide an interference fit therebetween. In some example forms, the diameter of the internal conduit of the barrel 220 varies along its length, for example, at least partially varying or tapering along its length such that sufficient retraction of the lumen extension tip 246 within the internal conduit of the barrel 220 (see FIG. 17) will eventually cause the lumen extension tip 246 to become free from engagement with the internal conduit of the barrel 220. In some example forms, the outer peripheral surface 272 generally remains in contact with the outer surface of the internal conduit of the barrel 220.

For example, as depicted in FIG. 17, a non-ENFit connector IC is shown attempting to misconnect with the lumen extension tip 246. As the ISO 80369-3 standard facilitates a reduction of misconnections between different enteral connectors, configuring the lumen extension tip 246 to be a separate piece can further reduce or de-risk the likelihood of a misconnection, for example, whereby attempting to connect the non-EN Fit connector IC to the tip 246 causes the lumen extension tip 246 to retract within the internal conduit of the barrel 220. In example forms, with the lumen extension tip 246 being movable within the internal conduit of the barrel 220, in the event of a user incorrectly attempting to couple non-ENFit connectors with the coupling 240 (and lumen extension tip 246 thereof), such misconnection is substantially (if not entirely) prevented, for example, since direct engagement with the lumen extension tip 246 causes retraction of the tip 246 relative to the internal conduit of the barrel 220. And thus, with the lumen extension tip 246 retracted within the internal conduit of the barrel, the syringe is incapable of properly functioning and thereby warning a user of the potential misconnection and/or preventing non-ENFit connectors from being unintentionally misconnected with the lumen extension tip. In example forms, the force required to cause retraction of the lumen extension tip 246 can be adjusted based on the interference provided between the lumen extension tip 246 (and the base 270 thereof) and the internal conduit of the barrel 220 (or with other portions of the syringe). For example, according to some example forms, only a relatively small force is required to cause retraction of the lumen extension tip 246. Alternatively, in other example forms, a larger force is required to cause retraction of the lumen extension tip 246 within the internal conduit of the barrel 220. Preferably, the interference provided between the lumen extension tip and the syringe can be adjusted as desired such that the desired force causes retraction of the lumen extension tip within the internal conduit of the barrel.

As depicted in FIGS. 19-21, the base 270 of the lumen extension tip 246 can preferably be configured in various forms such that coupling and/or sealing engagement is provided between the base 270 (or at least a portion of the lumen extension tip 246) and the internal conduit of the barrel 220 or platform 243. FIG. 19 shows the lumen extension tip 246 seated within the internal cavity and projecting coaxially within the coupling 240. In example embodiments, the base 270 comprises an outwardly curved peripheral surface 272a for engagement with a radiused recess formed in the outer surface of the internal conduit of the barrel 220. In alternate example forms, the interengagement provided between the outwardly curved peripheral surface 272a and the radiused recess provides a sufficient seal therebetween (see FIG. 19), and preferably provides for sufficient seating engagement therebetween. In some example forms, the interference between the outwardly curved peripheral surface 272a and the radiused recess is such that a non-ENFit connector attempting to misconnect with the lumen extension tip 246 causes the base 270 and the outwardly curved peripheral surface 272a of the lumen extension tip 246 to disengage the radiused recess and begin to move rearwardly within the internal lumen of the barrel 220 (e.g., similar to the tip 24 of FIG. 17).

Alternatively, as depicted in FIG. 20, the base 270 of the lumen extension tip 246 comprises an inwardly directed outer peripheral surface 272b for interengagement with a radiused ring or rib of the outer surface of the internal cavity of the barrel 220. Optionally, a seal ring 280 is provided between the abutment surface 274 and the upper surface 243a. According to another example form, a protruding rib or ring 282 extends from the abutment surface 274 for interengagement within a circular recess formed within a portion of the platform 243 (see FIG. 21). Optionally, according to other example embodiments, the lumen extension tip 246 (e.g., cylindrical body and/or base) can be shaped and sized as desired, and can be configured for removable or permanent interengagement with the internal lumen of the barrel (or other portions of the syringe). Optionally, as described above, the interengagement between the lumen extension tip and the syringe is such that an attempted misconnection with a non-ENFit connector is de-risked by retraction of the lumen extension tip within the internal conduit of the barrel 220. In example embodiments, with the lumen extension tip 246 being separate and movable with respect to the syringe, the likelihood of non-ENFit connectors being unintentionally misconnected with the lumen extension tip 246 is substantially reduced. As such, the incidence of potential misconnections with other coupling formats, for example, luer slip couplings or other coupling formats, can be reduced or avoided. For example, in example forms, attempting to connect other coupling formats that are not configured according to a coupling substantially conforming to ISO 80369-3 design standard will cause the lumen extension tip 246 to move within the syringe, and thus, provide a warning the user and/or will not allow for connecting with the non-ENFit coupling format.

According to other example embodiments, the lumen extension tip 246 can comprise one or more engagement features for providing interengagement with the internal conduit of the barrel 220 (or other portions of the syringe 200), and the plunger movably mounted within the barrel 220 can preferably provide for manipulating or facilitating movement of the lumen extension tip 246 within the internal conduit of the barrel 220, for example, to provide for selective engagement/disengagement of the lumen extension tip 246 within the internal conduit of the barrel 220. According to example forms, one or more teeth or coupling features are provided on a portion of the base 270 for engagement with a portion of the plunger. And, one or more interengagement features are provided with the lumen extension tip 246 for coupling engagement with the internal conduit of the barrel 220 (or other portions of the syringe). Thus, according to some example forms, the plunger can engage the one or more coupling features of the base 270 such that the lumen extension tip 246 can be manipulated (or rotationally driven) to provide for selective engagement/disengagement of the lumen extension tip 246 with the syringe 200.

Figure 22:
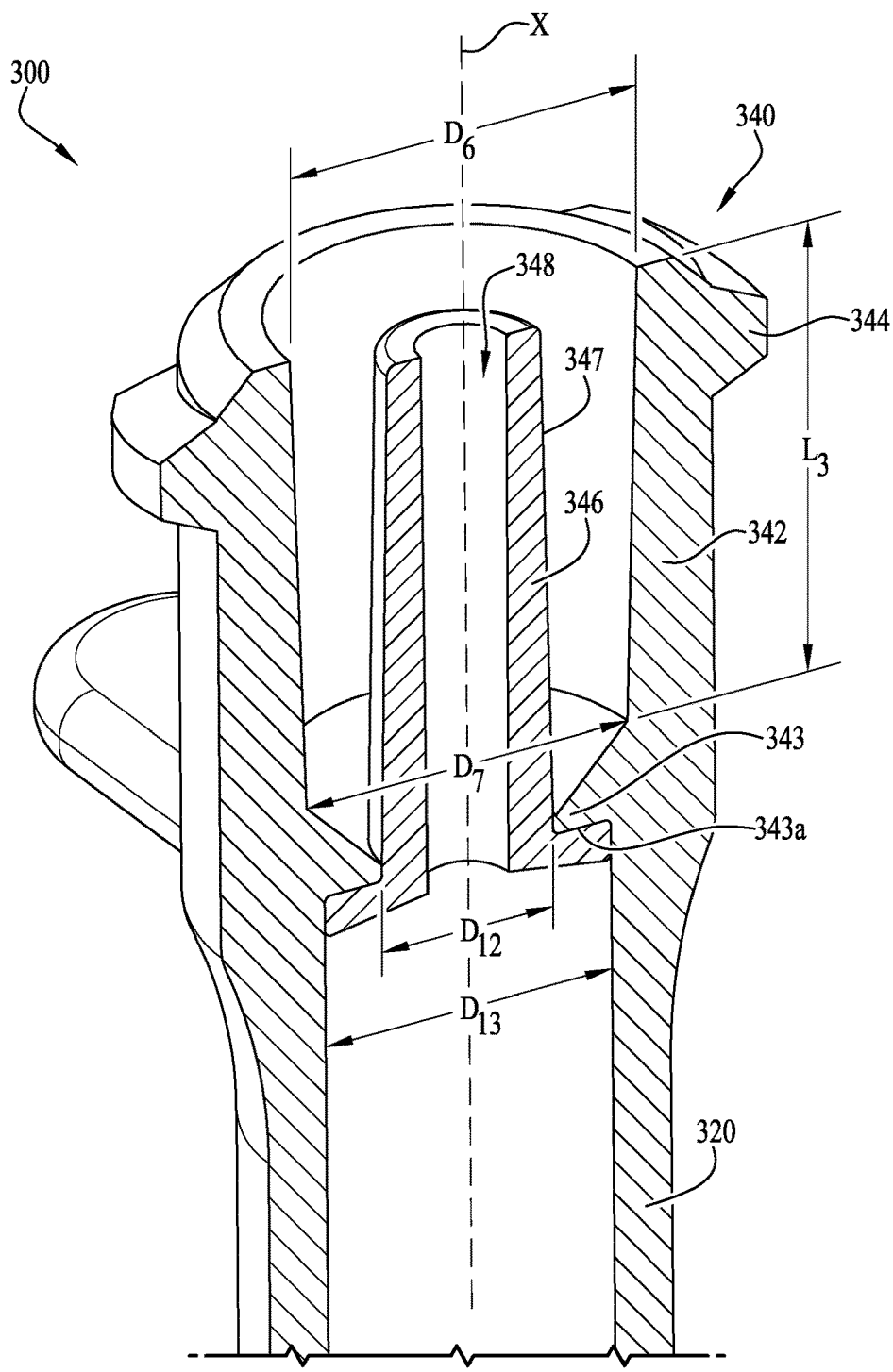
FIG. 22 is a perspective cross-sectional view of a portion of a syringe including an enteral dosing control coupling having a lumen extension tip seated and fully extending from the end of the syringe according to another example embodiment of the present invention.
Figure 23:
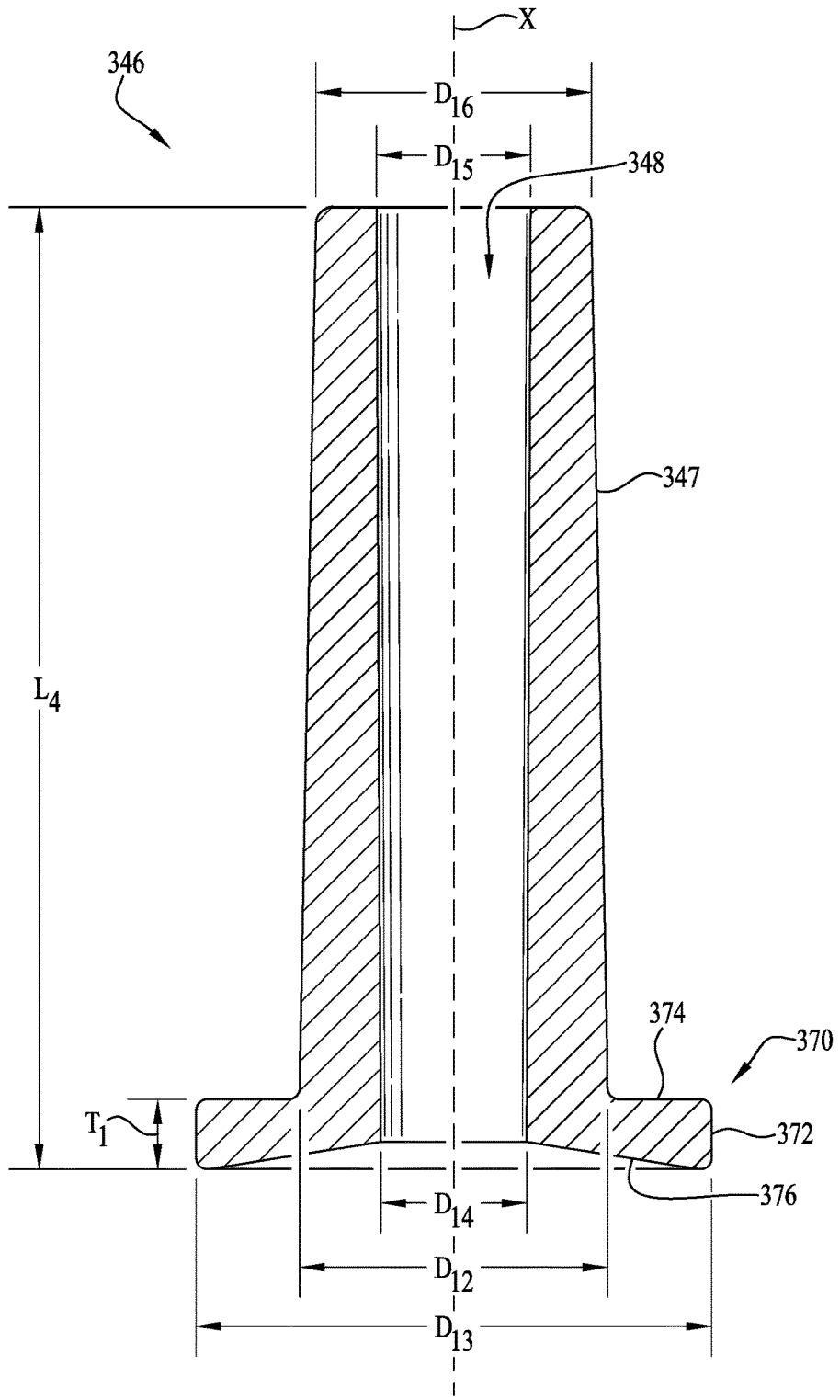
FIG. 23 is a cross-sectional view of the lumen extension tip portion of the syringe of FIG. 22.

FIGS. 22-23 show a syringe 300 comprising a lumen extension tip 346 according to another example embodiment of the present invention. In example embodiments, the syringe 300 is generally similar to the syringe 200 as described above. In example forms, the first and second internal diameters D6, D7 of the collar 340 and the length L3 defined therebetween are substantially similar as described above. For example, the first internal diameter D6 is about 5.69 millimeters, the second internal diameter D7 is about 5.26 millimeters, and the length L3 defined between the first and second internal diameters D6, D7 is about 7.14 millimeters. In example embodiments, the diameter D12 of the central opening of the syringe 300 (e.g., for receiving the lumen extension tip 346) is about 2.80 millimeters, and the diameter D13 of the internal conduit of the syringe barrel 320 is about 4.69 millimeters. Like the embodiment illustrated in FIGS. 2 and 5, the collar 340 comprises a pair of helical coupling lugs 344 projecting outwardly from the exterior surface of the collar.

As depicted in FIG. 23, the lumen extension tip 346 is generally similarly shaped as described above and comprises a cylindrical body having a base 370 at an end thereof and comprising an internal lumen 348 extending entirely through the cylindrical body. In example forms, the outer diameter D13 of the internal conduit of the barrel 320 is substantially similar to the outer diameter D13 of the base 370, for example, which is about 4.69 millimeters. Thus, according to example embodiments, the outer diameter D13 of the base 370 is sized to provide for an interference, frictional fit with the internal conduit of the barrel 320. The base 370 comprises a thickness T1 of about 0.64 millimeters and the outer peripheral surface 372 is generally substantially flat and generally parallel relative to the axis X longitudinally extending along a length L4 of the tip 346. A bottom side 376 of the base 370 comprises a slightly tapered surface that is generally angled towards the opening of the internal conduit 348. In example embodiments, the length L4 (defined between the ends of the tip 346) is about 8.76 millimeters. As similarly described above, the base 370 of the tip 346 comprises an abutment surface 374 for engagement with the upper surface 343a of the platform 343. The internal conduit 348 of the tip 346 comprises a first inner diameter D14 defined near the base 370 and a second inner diameter D15 the end of the tip. In example embodiments, the first inner diameter is about 1.33 millimeters and the second inner diameter D15 is about 1.40 millimeters. The outer diameter of the end of the tip 346 defines an outer diameter D16, which is about 2.51 millimeters according to one example form. In example forms, the outer periphery of the cylindrical body of the tip 346 comprises a surface 347 that is provided for fitting within the internal cavity of a male hub H of an ISO 80369-3 compatible connector. In example forms, the end of the tip 346 generally near the outer diameter D16 con comprise a radiused edge or other curved or tapered feature. As depicted, a radiused edge is provided at the end portion of the tip 346.

FIGS. 24-27 show syringes 400, 500 comprising lumen extension tips 446, 546 according to additional example embodiments of the present invention. In example embodiments, the dosing control couplings (as described above) can be adapted for use with syringes of different sizes. For example, FIGS. 24-25 depicts a 3 milliliter syringe 400 comprising a syringe body 420, an ISO 80369-3 compatible enteral dosing control coupling 440 in the form of a modified female ENFit coupling. The lumen extension tip 446 can be integrally formed with the coupling as depicted, or in alternate forms can be a separate component. Similarly, FIGS. 26-27 show a 6 milliliter syringe 500 comprising a syringe body 520, an ISO 80369-3 compatible enteral dosing control coupling 540 in the form of a modified female ENFit coupling positioned offset from the barrel of the syringe. The lumen extension tip 446 can be integrally formed with the coupling. Alternatively, the lumen extension tips 446, 546 can be separate and movable with respect to the syringe, for example, as described above with respect to FIGS. 12-23. In example embodiments, the enteral dosing control couplings 440, 540 of the syringes 400, 500 can be applied to syringes of various volumes and shapes, for example, between about 0.5 milliliters-6 milliliters and wherein the dosing control couplings can be positioned concentrically, off-centered, or asymmetrical relative to the syringe body. In still other embodiments, a low-dose tip or dosing control coupling according to any of the embodiments as disclosed herein can be provided in connection with various other syringe formats including, for example syringes having non-circular barrel configurations (see U.S. patent application Ser. No. 14/224,297, incorporated herein by reference). Similarly to the embodiment illustrated in FIGS. 1-5, the lumen extension tip 446, 546 includes an internal surface defining the lumen or fluid delivery conduit 448, 548, a positioning flange 422 extends transversely outward from the barrel 420, a base flange 430, 530 is at a distal end of the barrel, the coupling 440, 540 comprises a cylindrical outer collar 442, 542 defining a hollow internal chamber, and a pair of helical coupling lugs 444, 544 projecting outwardly from the exterior surface of the collar.

While the invention has been described with reference to example embodiments, it will be understood by those skilled in the art that a variety of modifications, additions and deletions are within the scope of the invention, as defined by the following claims.

What is claimed is:

1. An enteral dosing control coupling comprising a cylindrical collar defining a hollow internal chamber comprising an internal diameter and having a smooth interior surface, and a lumen extension tip defining a cylindrical body comprising a base end with an outer diameter of about 2.85 millimeters and a fluid-delivery end having a smooth outer surface and comprising an internal lumen extending axially through the cylindrical body, the lumen extension tip being positioned concentrically and coaxially within the cylindrical collar such that the cylindrical body projects axially into the hollow internal chamber, wherein the lumen extension tip fluid-delivery end does not extend beyond an end of the cylindrical collar, and external coupling members formed on a portion of the cylindrical collar, the external coupling members being configured for coupling engagement with an ISO 80369-3 compatible coupling;

wherein the internal diameter of the cylindrical collar is greater than the outer diameter of the cylindrical body of the lumen extension tip such that a space defined therebetween forms a receiver for receiving a cooperating portion of the ISO 80369-3 compatible coupling, wherein the enteral dosing control coupling is configured such that, upon engagement of the enteral dosing control coupling with the cooperating portion of the ISO 80369-3 compatible coupling, the hollow internal chamber is occupied by the cooperating portion of the ISO 80369-3 compatible coupling, from the smooth interior surface of the cylindrical collar to the smooth outer surface of the lumen extension tip, with an outer surface of the cooperating portion of the ISO 80369-3 compatible coupling engaging with at least a portion of the smooth interior surface of the cylindrical collar, and with an inner surface of the cooperating portion of the ISO 80369-3 compatible coupling engaging with at least a portion of the smooth outer surface of the extension tip.

2. The enteral dosing control coupling of claim 1, wherein the ISO 80369-3 compatible coupling comprises a hub centrally positioned therein and defining an internal conduit extending therethrough.

3. The enteral dosing control coupling of claim 2, wherein the lumen extension tip is sized, shaped and positioned within the cylindrical collar for compatible fitting engagement within the internal conduit of the hub of the ISO 80369-3 compatible coupling.

4. The enteral dosing control coupling of claim 1, wherein the lumen extension tip defines a contained volume of between about 0.005 milliliters to about 0.03 milliliters.

5. The enteral dosing control coupling of claim 4, wherein the lumen extension tip defines a contained volume of about 0.01 milliliters.

6. The enteral dosing control coupling of claim 1, wherein the lumen extension tip is integrally formed with the cylindrical collar.

7. An enteral fluid device comprising the enteral dosing control coupling of claim 1.

8. The enteral fluid device of claim 7, selected from a syringe, an enteral fluid collection device, an enteral fluid storage device, an enteral fluid delivery tube or an enteral fluid delivery conduit.

9. An enteral syringe comprising:
a hollow cylindrical barrel adapted to receive a plunger for retraction and advancement within the syringe barrel to transfer a delivered fluid to and from a contained volume of the syringe barrel, and further comprising a cylindrical coupling collar extending from a proximal end of the syringe barrel, the cylindrical coupling collar defining a hollow internal chamber having a smooth interior surface and comprising at least one external coupling member formed on an exterior portion of the cylindrical collar; and
an enteral dosing control coupling comprising the cylindrical coupling collar defining the hollow internal chamber comprising an internal diameter, and a lumen extension tip defining a cylindrical body comprising a base end with an outer diameter of about 2.85 millimeters and a fluid-delivery end, having a smooth outer surface and comprising an internal lumen extending axially through the cylindrical body, the lumen extension tip being positioned concentrically and coaxially within the cylindrical coupling collar such that the cylindrical body projects axially into the hollow internal chamber, wherein the lumen extension tip fluid-delivery end does not extend beyond an end of the cylindrical coupling collar,
wherein the at least one external coupling member being configured for coupling engagement with an ISO 80369-3 compatible coupling;
wherein the internal diameter of the cylindrical coupling collar is greater than the outer diameter of the cylindrical body of the lumen extension tip such that a space defined therebetween forms a receiver for receiving a cooperating portion of the ISO 80369-3 compatible coupling,
wherein the coupling is configured such that, upon engagement of the enteral dosing control coupling with the cooperating portion of the ISO 80369-3 compatible coupling, the hollow internal chamber is occupied by the cooperating portion of the ISO 80369-3 compatible coupling, from the smooth interior surface of the cylindrical coupling collar to the smooth outer surface of the lumen extension tip, with an outer surface of the cooperating portion of the ISO 80369-3 compatible coupling engaging with at least a portion of the smooth interior surface of the cylindrical coupling collar, and with an inner surface of the cooperating portion of the ISO 80369-3 compatible coupling engaging with at least a portion of the smooth outer surface of the lumen extension tip.

10. The enteral syringe of claim 9, wherein the cylindrical collar is shaped and sized according to the ISO 80369-3 standard.

11. The enteral syringe of claim 10, wherein the lumen extension tip is integrally formed with the proximal end of the syringe barrel.

* * * * *